US011141090B2

(12) United States Patent
Shikii et al.

(10) Patent No.: US 11,141,090 B2
(45) Date of Patent: Oct. 12, 2021

(54) HUMAN-STATE ESTIMATING METHOD AND HUMAN-STATE ESTIMATING SYSTEM

(71) Applicant: Panasonic Intellectual Property Management Co., Ltd., Osaka (JP)

(72) Inventors: Shinichi Shikii, Nara (JP); Koichi Kusukame, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 920 days.

(21) Appl. No.: 15/184,976

(22) Filed: Jun. 16, 2016

(65) Prior Publication Data
US 2016/0374606 A1 Dec. 29, 2016

(30) Foreign Application Priority Data

Jun. 29, 2015 (JP) .............................. JP2015-130300
Feb. 24, 2016 (JP) .............................. JP2016-033639

(51) Int. Cl.
A61B 5/18 (2006.01)
A61B 5/01 (2006.01)
(Continued)

(52) U.S. Cl.
CPC .............. *A61B 5/18* (2013.01); *A61B 5/0077* (2013.01); *A61B 5/015* (2013.01);
(Continued)

(58) Field of Classification Search
CPC ......... A61B 5/01; A61B 5/015; A61B 5/0077; A61B 5/02055; A61B 5/165; A61B 5/18;
(Continued)

(56) References Cited

U.S. PATENT DOCUMENTS 5,689,241 A * 11/1997 Clarke, Sr. ................ A61B 5/18
340/575
7,027,621 B1 * 4/2006 Prokoski ............ G06K 9/00248
180/272
8,172,155 B2 * 5/2012 Nakayama ................ A61B 5/01
236/46 R
2008/0243027 A1 10/2008 Nakayama et al.
(Continued)

FOREIGN PATENT DOCUMENTS

CN 101547643 A 9/2009
JP 6-265189 A 9/1994
(Continued)

OTHER PUBLICATIONS

Inoue et al. JP H09154835A. Google Patents Japanese to English Machine Translation. Jun. 17, 1997. Translated generated Jun. 10, 2019. (Year: 2019).*
(Continued)

*Primary Examiner* — Devin B Henson
(74) *Attorney, Agent, or Firm* — Greenblum & Bernstein, P.L.C.

(57) ABSTRACT

A human-state estimating method includes: obtaining a thermal sensation index obtained by indexing, in a specified range, an estimated thermal sensation of a person; determining whether or not the obtained thermal sensation index is in a predetermined range in the specified range; and estimating a human state, which is a state of the person, based on a physiological amount in which an activity of an autonomic nervous system of the person is reflected, the physiological amount being obtained when it is determined that the obtained thermal sensation index is in the predetermined range.

15 Claims, 23 Drawing Sheets

(51) Int. Cl.
*A61B 5/0205* (2006.01)
*A61B 5/00* (2006.01)
*A61B 5/16* (2006.01)
*G08B 21/06* (2006.01)
*B60W 40/08* (2012.01)

(52) U.S. Cl.
CPC .......... *A61B 5/02055* (2013.01); *A61B 5/165* (2013.01); *A61B 5/4005* (2013.01); *A61B 5/6893* (2013.01); *A61B 5/7278* (2013.01); *G08B 21/06* (2013.01); *B60W 40/08* (2013.01); *B60W 2040/0818* (2013.01); *B60W 2040/0827* (2013.01); *B60W 2040/0872* (2013.01)

(58) Field of Classification Search
CPC ... A61B 5/4005; A61B 5/6893; A61B 5/7278; G01K 13/002; G01K 13/004; B60K 28/06; B60K 28/066
See application file for complete search history.

(56) References Cited

U.S. PATENT DOCUMENTS

| | | |
|---|---|---|
| 2010/0049066 A1 | 2/2010 | Hatakeyama |
| 2010/0217137 A1* | 8/2010 | Kanai ...................... A61B 5/18 600/500 |
| 2014/0313309 A1* | 10/2014 | Matsuo .................... A61B 5/01 348/78 |
| 2015/0094914 A1* | 4/2015 | Abreu ................ B60H 1/00742 701/41 |

FOREIGN PATENT DOCUMENTS

| | | |
|---|---|---|
| JP | 9-154835 | 6/1997 |
| JP | 2000-104972 A | 4/2000 |
| JP | 2002-120591 | 4/2002 |
| JP | 2008-241135 A | 10/2008 |

OTHER PUBLICATIONS

English Translation of Chinese Search Report dated Apr. 8, 2020 for the related Chinese Patent Application No. 201610405975.1.

* cited by examiner

FIG. 4

- +3    HOT
- +2    WARM
- +1    SLIGHTLY WARM
- 0    NEITHER HOT NOR COLD (THERMONEUTRAL POINT)
- −1    SLIGHTLY COOL
- −2    COOL
- −3    COLD

FIG. 8

- 5    VERY SLEEPY
- 4    RATHER SLEEPY
- 3    SLEEPY
- 2    SLIGHTLY SLEEPY
- 1    NOT SLEEPY

NOSTRIL PARTS

HUMAN-STATE ESTIMATING METHOD AND HUMAN-STATE ESTIMATING SYSTEM

BACKGROUND

1. Technical Field

The present disclosure relates to a human-state estimating method and a human-state estimating system.

2. Description of the Related Art

It is said that the state of a degree of stress, sleepiness, or the like the human feels (hereinafter may be referred to as a "human state") is associated with a physiological amount based on the activity of the human autonomic nervous system. Examples of the physiological amount based on the activity of the autonomic nervous system include a skin temperature, fluctuations in heartbeat intervals, and a respiration waveform. For example, the skin temperature, which is a physiological amount, is explained by a mechanism in which when the human feels stress, the sympathetic nervous system of the autonomic nervous system increases its activity to constrict the blood vessels of the peripheral parts to reduce the blood flow therein, so that the skin temperatures of the peripheral parts decreases. Also, the sleepiness, which is a physiological amount, is explained by a mechanism in which when the human feels sleepy, the parasympathetic nervous system of the autonomic nervous system increases its activity to relax the blood vessels of the peripheral parts to increase the blood flow therein, so that the skin temperatures of the peripheral parts increase. Dozing detecting devices utilizing the above-described mechanisms have been disclosed (see, for example, Japanese Unexamined Patent Application Publication No. 9-154835 and Japanese Unexamined Patent Application Publication No. 2002-120591).

SUMMARY

In one general aspect, the techniques disclosed here feature a human-state estimating method that includes: obtaining a thermal sensation index obtained by indexing, in a specified range, an estimated thermal sensation of a person; determining whether or not the obtained thermal sensation index is in a predetermined range in the specified range; and estimating a human state, which is a state of the person, based on a physiological amount in which an activity of an autonomic nervous system of the person is reflected, the physiological amount being obtained when it is determined that the obtained thermal sensation index is in the predetermined range.

According to the human-state estimating method in the present disclosure, the accuracy of estimating the human state improves.

It should be noted that general or specific embodiments may be implemented as a system, a method, an integrated circuit, a computer program, a computer-readable recording medium such as a compact disc read-only memory (CD-ROM), or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4 illustrates an example of a thermal sensation index in the first embodiment;

FIG. 8 illustrates an example of a sleepiness index in the first embodiment;

DETAILED DESCRIPTION (Knowledge Underlying Present Disclosure)

Figure 1A:
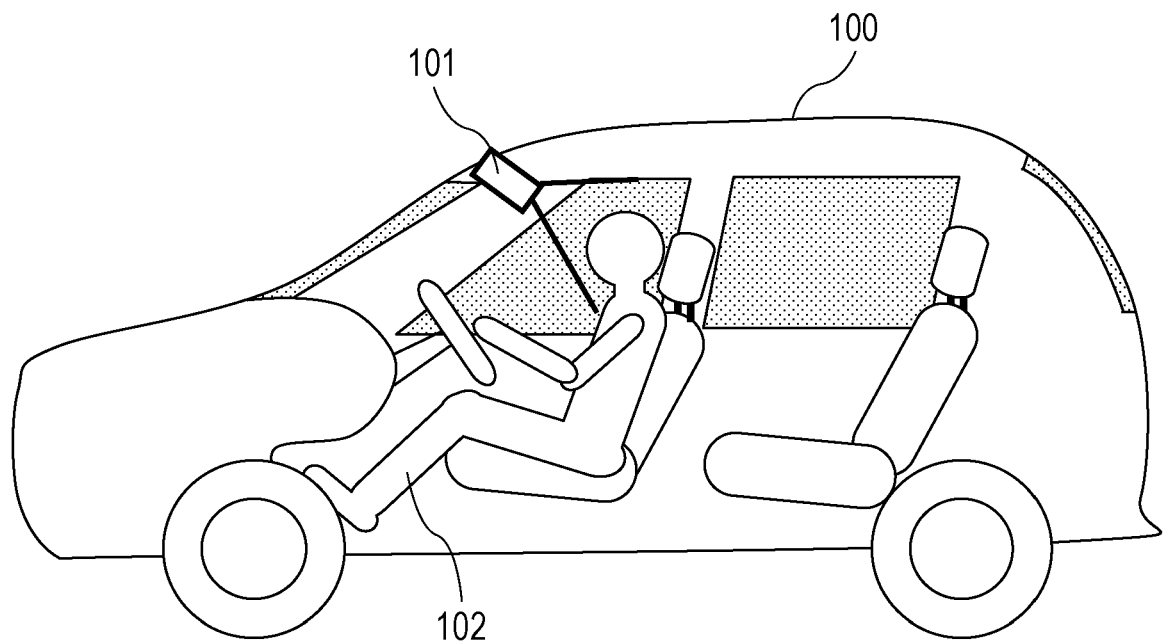
FIG. 1A is a conceptual diagram of a vehicle in which a human-state estimating device in a first embodiment is provided.

The human organs are not actively controlled by the human's will and are controlled through the autonomic nervous system by central neurons of the brain on the basis of information from receptors that exist throughout the body. The autonomic nervous system is constituted by two systems, namely, the sympathetic nervous system and the parasympathetic nervous system, and both of the systems control one organ in many cases.

For example, when the sympathetic nervous system increases its activity, a heart rate increases, and variations in the heartbeat intervals decrease. On the other hand, when the parasympathetic nervous system increases its activity, the heart rate decreases, and variations in the heartbeat intervals increase. Also, when the sympathetic nervous system increases its activity, peripheral blood vessels are constricted to impede blood flow, so that the skin temperatures of peripheral parts decrease. In contrast, when the parasympathetic nervous system increases its activity, the blood vessels are relaxed to promote blood flow, so that the skin temperatures of the peripheral parts increase.

The reason why the peripheral skin temperatures decrease under stress is thought to be that the activity of the sympathetic nervous system is increased to feed blood flows to the core parts of the body and to further increase the heart rate to thereby cause a large amount of blood to flow to the brain and muscles to supply oxygen thereto, vitalizing the activities of the brain and the muscles. Also, the reason why the peripheral skin temperatures increase owing to sleepiness is thought to be that, since the core body temperature during sleep needed to be reduced to a temperature slightly lower than the temperature during wakefulness, the activity of the parasympathetic nervous system is activated to supply blood flows throughout the peripheral parts to thereby facilitate that the body temperature decreases.

An increase in the activity of the sympathetic nervous system or the parasympathetic nervous system is affected by the human thermal sensation (i.e., the human's sensation of hotness or coldness), other than the above-described influences of stress or sleepiness. For example, when the human feels hot, it is necessary to promote heat release from the body, and thus the parasympathetic nervous system increases its activity in order to relax the blood vessels of the peripheral parts. As a result, the heart rate decreases, and variations in the heartbeat intervals increase. In contrast, when the human feels cold, it is necessary to suppress heat release from the body, and thus the sympathetic nervous system increases its activity in order to constrict the blood vessels of the peripheral parts. As a result, the heart rate increases, and variations in the heartbeat intervals decrease. Thus, when the human state, such as stress or sleepiness, is estimated on the basis of a physiological amount, such as a skin temperature or heartbeat intervals, based on the activity of the autonomic nervous system, it is necessary to determine whether the physiological amount is due to an influence of stress or sleepiness or due to an influence of a variation in the thermal sensation.

That is, since the activity of the autonomic nervous system receives influences other than the influence of stress or sleepiness, further study is required in order to accurately estimate the human state, such as the degree of stress or sleepiness.

The present disclosure provides a human-state estimating method for improving the accuracy of the human state.

A human-state estimating method according to one aspect of the present disclosure includes: obtaining a thermal sensation index obtained by indexing, in a specified range, an estimated thermal sensation of a person; determining whether or not the obtained thermal sensation index is in a predetermined range in the specified range; and estimating a human state, which is a state of the person, based on a physiological amount in which an activity of an autonomic nervous system of the person is reflected, the physiological amount being obtained when it is determined that the obtained thermal sensation index is in the predetermined range.

With this arrangement, false detection during human state estimation is reduced, thereby making it possible to estimate the human state with higher accuracy. More specifically, in the human-state estimating method according to one aspect of the present disclosure, the human state is estimated based on a physiological amount under a situation in which a condition that the obtained thermal sensation information is in a predetermined range is satisfied. Thus, false detection during human state estimation can be reduced, compared with a case in which the human state is estimated regardless of whether or not the condition is satisfied. Accordingly, the above-described human-state estimating method makes it possible to improve the accuracy of estimating the human state. In addition, for example, a reduction of false detection eliminates the need for performing the detection processing again, thus offering advantages in that the throughput, the processing load, and the amount of power consumed decrease.

For example, the predetermined range is a partial range of the specified range, the partial range including a thermoneutral point for thermal sensation.

According to this arrangement, when the human thermal sensation is in a range relatively close to a thermoneutral point at which the human feels neither hot nor cold, the human state is estimated. When the human feels hot or warm, the skin temperature increases through promotion of heat release from the body. In contrast, when the human feels cold or cool, the skin temperature decreases through suppression of heat release from the body. That is, when the human thermal sensation is in a range relatively close to the thermoneutral point, an influence of promotion or suppression of heat release from the human body is zero or relatively small. Hence, estimating the human state on the basis of the physiological amount in such a case can reduce the influence of promotion or suppression of heat release from the human body, the influence being included in the result of the estimation, and can contribute to preventing false detection and improving the estimation accuracy.

For example, the predetermined range is a partial range of the specified range, the partial range not including a point indicating being hottest as the thermal sensation and a point indicating being coldest as the thermal sensation.

According to this arrangement, when the human thermal sensation is in a range excluding a case in which the human feels very hot or very cold, the human state is estimated. When the human feels very hot, the heat release from the human body is greatly promoted. Also, when the human feels very cold, the heat release from the human body is greatly suppressed. Excluding such cases from cases in which the human state is estimated can reduce the influence of promotion or suppression of the heat release from the human body, the influence being included in the result of the estimation, and can contribute to preventing false detection and improving the estimation accuracy.

For example, the physiological amount is a nasal skin temperature of the person, and the human state includes a degree of sleepiness of the person.

According to this arrangement, when the degree of human sleepiness is estimated based on the human nasal skin temperature, it is possible to reduce the influence of promotion or suppression of heat release from his or her body, the influence being included in the result of the estimation. In addition, even when there is disturbance, use of the nasal skin temperature makes the estimation less susceptible to an influence of the disturbance.

For example, the thermal sensation index and the nasal skin temperature are obtained; in the determining, a determination is made as to whether or not the obtained thermal sensation index is in the predetermined range; and in the estimating of the human state, the degree of sleepiness of the person is estimated based on a range of an increase in the obtained nasal skin temperatures over time.

According to this arrangement, the degree of human sleepiness can be specifically estimated based on the human nasal skin temperature.

For example, the physiological amount includes a heartbeat interval of the person; and the human state is estimated based on a variation in the heartbeat interval as the obtained physiological amount.

According to this arrangement, the human state can be specifically estimated based on the human heartbeat interval.

For example, the physiological amount includes a respiration waveform of the person; and the human state is estimated based on the respiration waveform as the obtained physiological amount.

According to this arrangement, the human state can be specifically estimated based on the human respiration waveform. This can also contribute to reducing the processing load and increasing the processing speed.

For example, a skin temperature of an earlobe part of the person is obtained; in the obtaining of the thermal sensation index, a correlation between a skin temperature of an earlobe part and the thermal sensation index is used to obtain the thermal sensation index estimated based on the obtained skin temperature of the earlobe part; the physiological amount includes a pulse wave measured from the earlobe part of the person; and in the estimating of the human state, the human state is estimated based on frequency analysis of the obtained pulse wave.

According to this arrangement, the human state can be specifically estimated based on the skin temperature and the pulse wave of the human earlobe part. The earlobe part has a feature that the pulse wave can be easily measured. Accordingly, when a pulse wave is obtained from the earlobe part in conjunction with the skin temperature, information needed for estimating the human state can be obtained from the earlobe part at a time.

For example, in the obtaining of the thermal sensation index, the thermal sensation index estimated based on a predicted mean vote (PMV) is obtained.

For example, the specified range is represented by a seven-step evaluation scale for the PMV; and the predetermined range is a range in which a PMV value is −2 or more and is +2 or less in the specified range.

According to this arrangement, since the estimation is performed based on the PMV, the human thermal sensation can be more accurately estimated based on an air temperature, a humidity, an air speed, a radiant temperature, the amount of clothing, and the amount of activity, which are six thermal factors.

For example, the physiological amount is a nasal skin temperature of the person; the human state includes a degree of stress of the person; the thermal sensation index and the nasal skin temperature are obtained; in the determining, a determination is made as to whether or not the obtained thermal sensation index is in the predetermined range; and in the estimating of the human state, the degree of stress of the person is estimated based on a range of a decrease in the obtained nasal skin temperatures over time.

According to this arrangement, the degree of human stress can be specifically estimated based on the human nasal skin temperature.

For example, the physiological amount includes a skin blood flow, a blood pressure, or a pulse-wave propagation time of the person; and the human state includes a degree of sleepiness of the person.

According to this arrangement, the degree of human sleepiness can be specifically estimated based on the human skin blood flow, blood pressure, or pulse-wave propagation time.

For example, at least one of the obtaining, the determining, and the estimating may be performed using a processor.

A human-state estimating system according to one aspect of the present disclosure includes: a thermal sensation estimator that obtains a thermal sensation index obtained by indexing, in a specified range, an estimated thermal sensation of a person; a determiner that determines whether or not the obtained thermal sensation index is in a predetermined range in the specified range; and a human state estimator that estimates a human state, which is a state of the person, based on a physiological amount in which an activity of an autonomic nervous system of the person is reflected, the physiological amount being obtained when it is determined that the obtained thermal sensation index is in the predetermined range.

The human-state estimating system offers advantages that are the same as or similar to those of the above-described human-state estimating method.

For example, at least one of the thermal sensation estimator, the determiner, and the human state estimator may include a processor.

In addition, a non-transitory recording medium storing a program according to one aspect of the present disclosure is a non-transitory recording medium storing a program for causing a computer to execute the above-described human-state estimating method.

The non-transitory recording medium storing a program causing a computer to execute operations includes: obtaining a thermal sensation index obtained by indexing, in a specified range, an estimated thermal sensation of a person; determining whether or not the obtained thermal sensation index is in a predetermined range in the specified range; and estimating a human state, which is a state of the person, based on a physiological amount in which an activity of an autonomic nervous system of the person is reflected, the physiological amount being obtained when it is determined that the obtained thermal sensation index is in the predetermined range.

It should be noted that general or specific embodiments may be implemented as a system, a method, an integrated circuit, a computer program, a computer-readable recording medium such as a CD-ROM, or any selective combination thereof.

Embodiments will be described below in detail with reference to the accompanying drawings.

The embodiments described below each represent a general or specific example. Numerical values, shapes, materials, constituent elements, the arrangement and connection of constituent elements, steps, the order of steps, and so on described in the embodiments below are examples, and are not intended to limit the present disclosure. Of the constituent elements in the embodiments described below, the constituent elements not set forth in the independent claims that represent the broadest concept will be described as optional constituent elements.

First Embodiment

In a first embodiment, a description will be given of a human-state estimating method and a human-state estimating device that improve the accuracy of assuming a human state. The "human state" as used herein refers to a concept including the degree of sleepiness or the degree of stress of a human. The human-state estimating device may also be referred to as a "human-state estimating system".

An example in which the human-state estimating device in the present embodiment is provided in a vehicle will be described below with reference to FIGS. 1A to 12D.

Figure 1B:
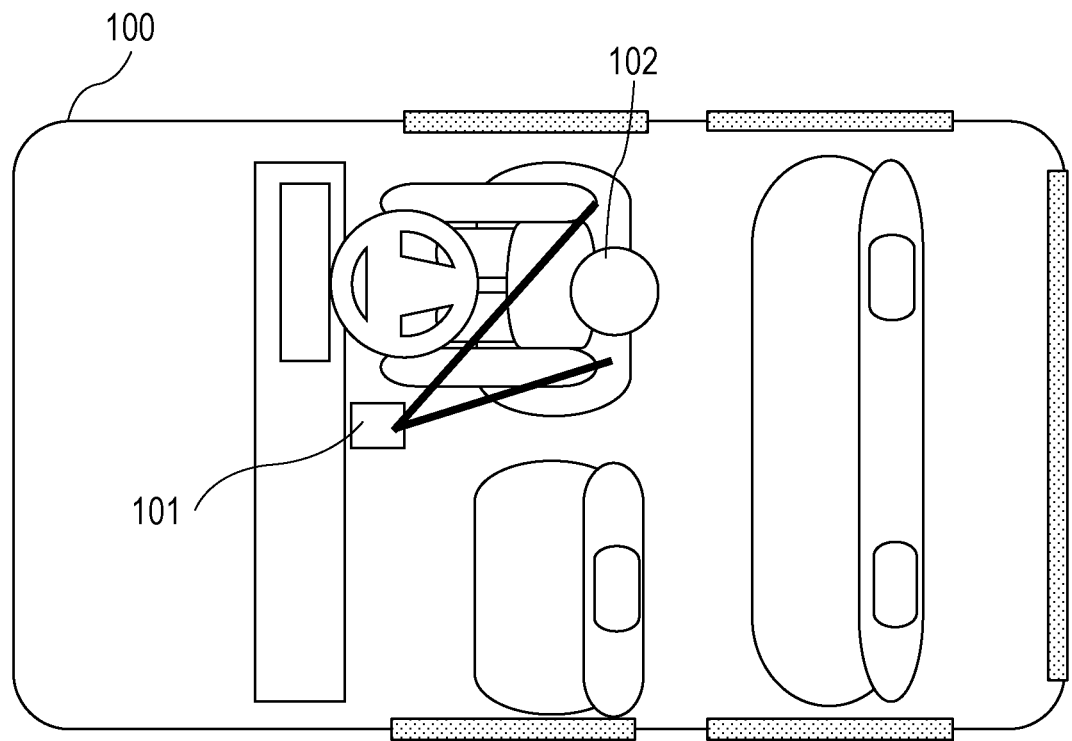
FIG. 1B is a schematic top view of the vehicle in which the human-state estimating device in the first embodiment is provided.

FIG. 1A is a conceptual diagram of a vehicle in which the human-state estimating device in the present embodiment is provided. FIG. 1B is a schematic top view of the vehicle in which the human-state estimating device in the present embodiment is provided.

A person 102 is in the driver's seat of a vehicle 100. The vehicle 100 has, in front of the driver's seat, a thermal image sensor 101 directed to the person 102, and can two dimensionally acquire a thermal distribution of the face of the person 102 and surroundings thereof. The thermal image sensor 101 typically has a structure in which elements, such as bolometers or thermopiles, that are sensitive to infrared light are arranged in a two-dimensional matrix, and the amount of infrared light emitted according to the temperature distribution of an object surface is formed on the elements, arranged in the matrix, by a lens to thereby make it possible to visualize the temperature distribution of the object surface.

Figure 2:
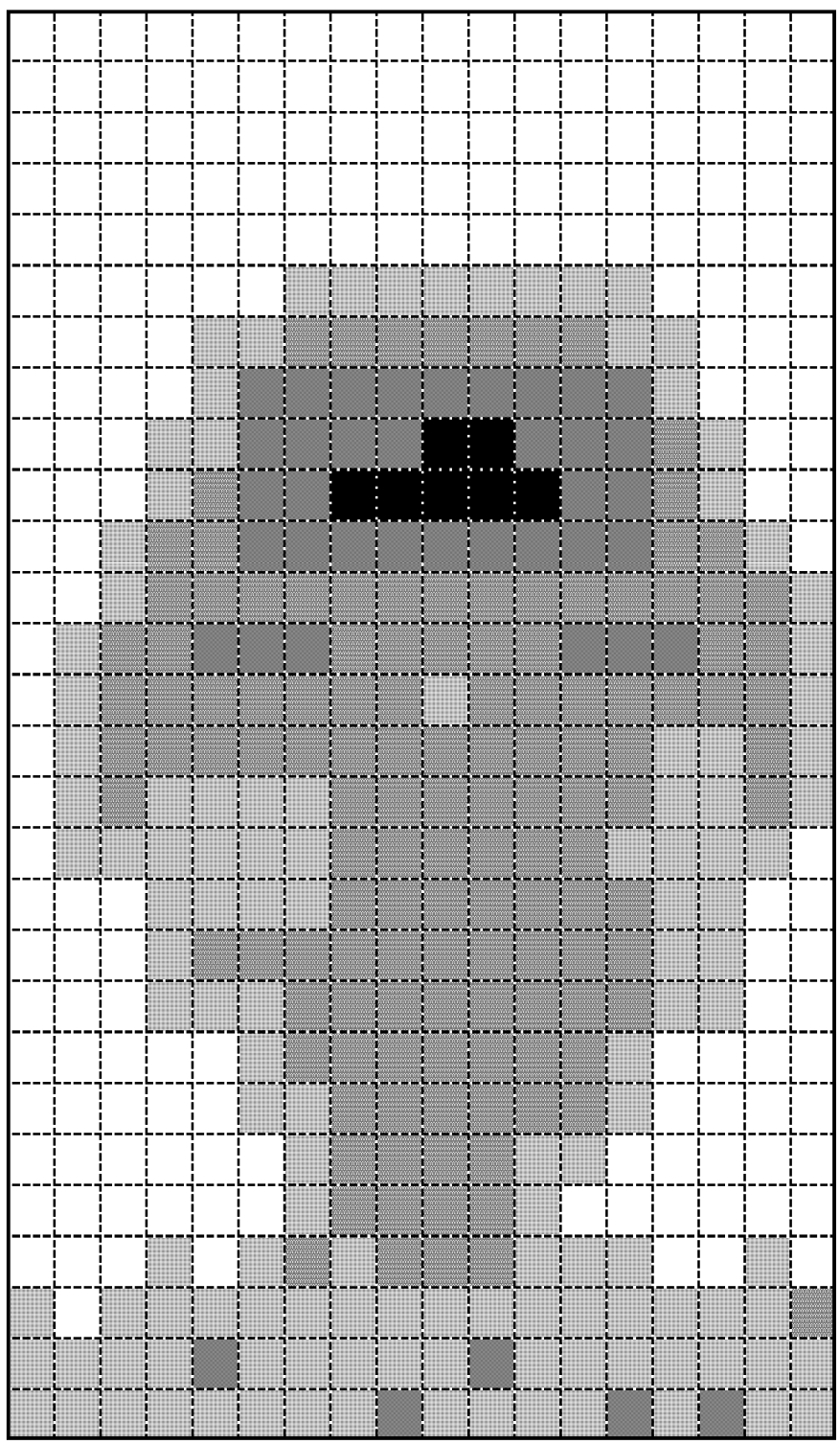
FIG. 2 illustrates one example of an image of a human face captured by a thermal image sensor in the first embodiment.

FIG. 2 illustrates one example of an image of a human face captured by the thermal image sensor 101 in the present embodiment.

When the thermal image sensor 101 and the person 102 has a positional relationship as illustrated in FIGS. 1A and 1B, for example, a thermal image as illustrated in FIG. 2 is captured. The thermal image illustrated in FIG. 2 is displayed such that portions (pixels) of an object that have higher temperatures have higher color densities. That is, the thermal image illustrated in FIG. 2 is displayed such that pixels having higher temperatures have colors closer to black, and thus it can be recognized that the temperatures in the vicinity of the forehead are high. The way the thermal image is displayed is not limited to this example. Also, the image acquired by the thermal image sensor 101 may be a still image or a moving image.

Figure 3:
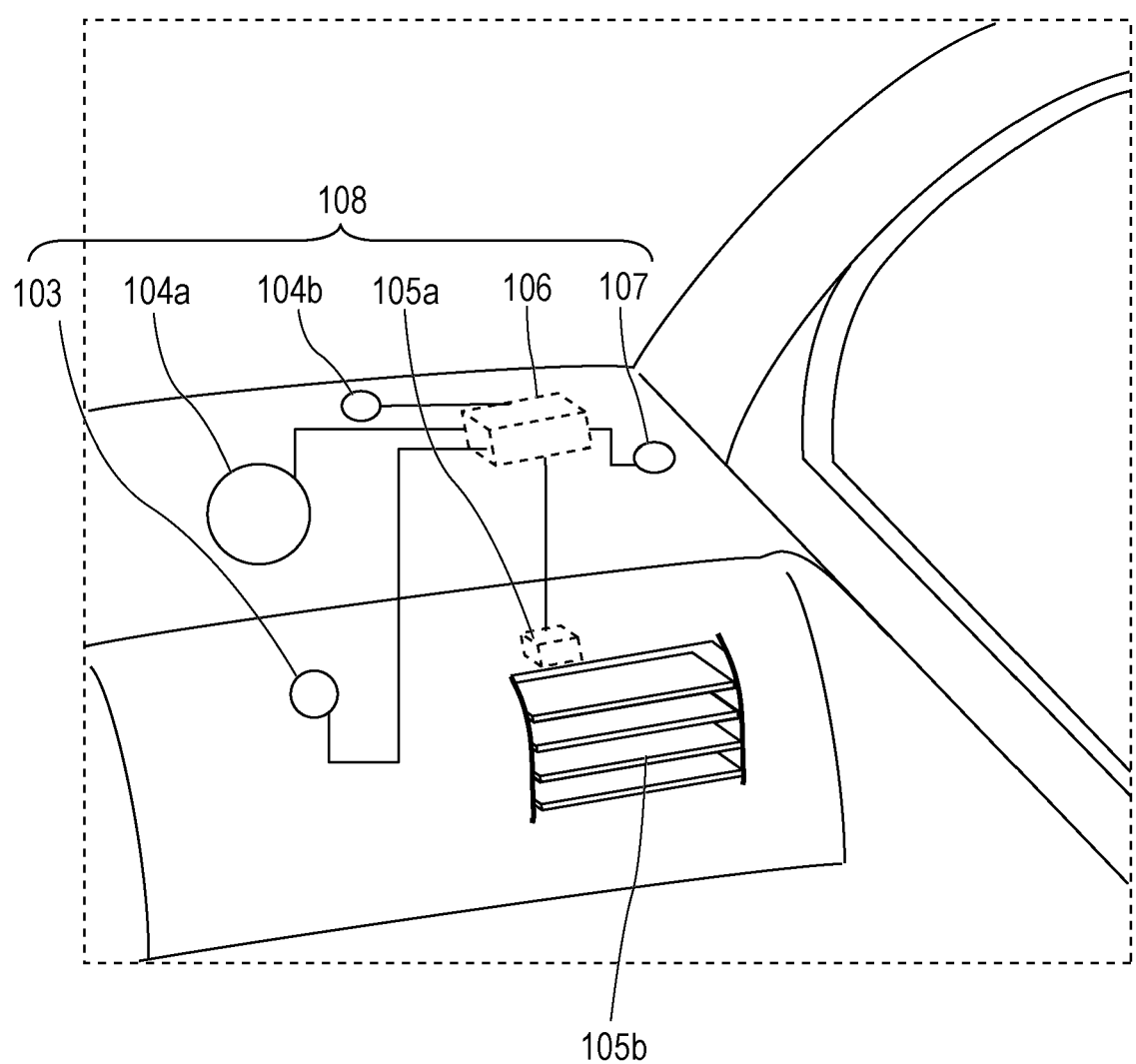
FIG. 3 is a schematic view of the configuration of a thermal sensation estimator in the first embodiment.
Figure 5:
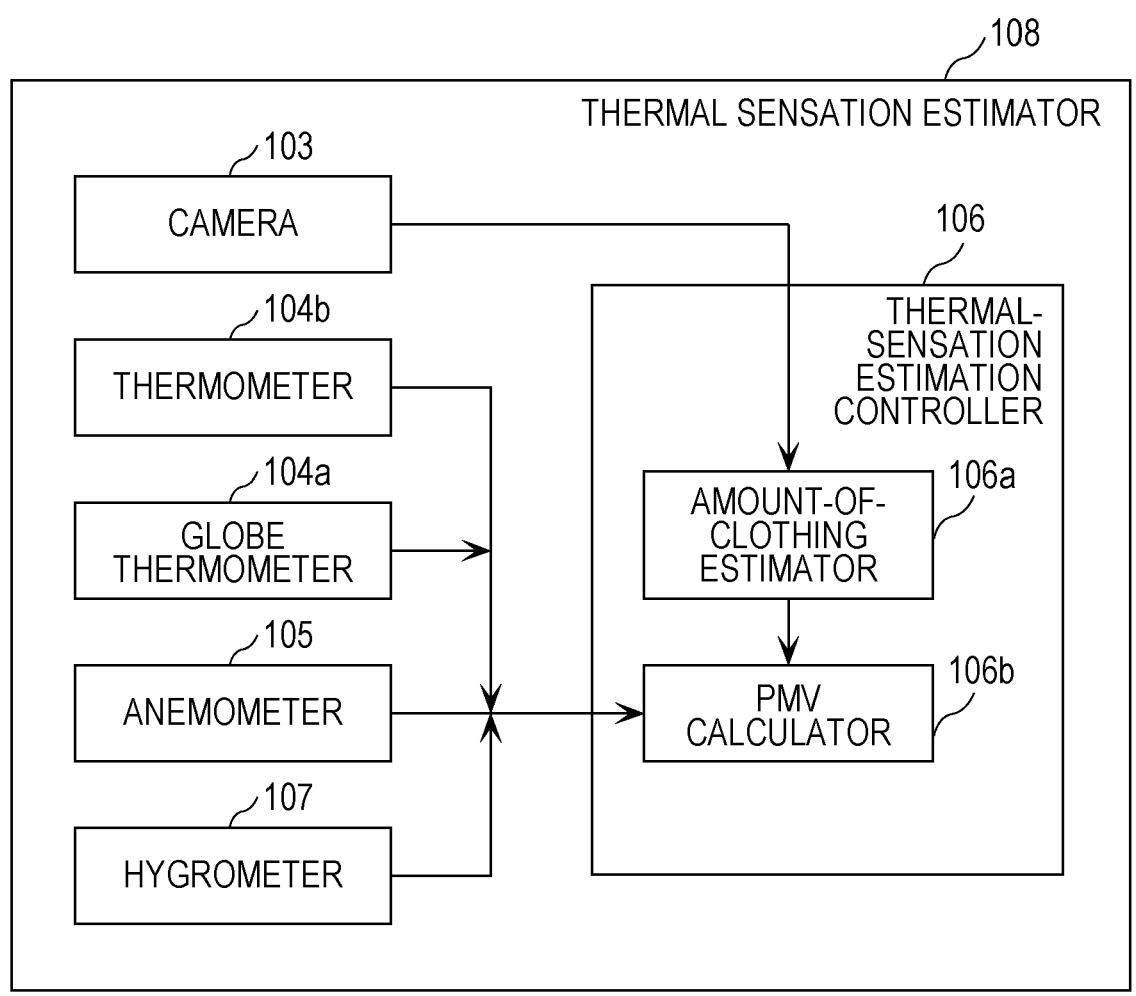
FIG. 5 is a block diagram illustrating functions of the thermal sensation estimator in the first embodiment.

FIG. 3 is a schematic view of the configuration of a thermal sensation estimator 108 in the present embodiment. FIG. 4 illustrates an example of a thermal sensation index in the present embodiment. FIG. 5 is a block diagram illustrating functions of the thermal sensation estimator 108 in the present embodiment. The thermal sensation estimator 108 provided in the vehicle 100 will be described with reference to FIGS. 3 to 5.

The human thermal sensation can be quantified, for example, using a seven-step index, as illustrated in FIG. 4. In this case, a thermal sensation of 0 is a thermoneutral point at which the human feels neither hot nor cold, and the human thermal sensation is quantified such that it takes a positive value whose absolute value is larger as the human feels hotter and conversely takes a negative value whose absolute value is larger as the human feels colder. Such a quantified thermal sensation (or an indexed thermal sensation) is referred to as a "thermal sensation index". The thermal sensation index may also be referred to simply as a "thermal sensation" as long as it does not cause confusion.

A scale that associates the thermal sensation with six thermal factors is the PMV. Thus, it is known that when six thermal factors, that is, an air temperature, a humidity, a radiant temperature, an air speed, the amount of human activity, and the amount of clothing, are known, it is possible to estimate the human thermal sensation by using a PMV calculation expression. A method for determining the thermal sensation by using the PMV will be described below in detail. The index for the human thermal sensation may be represented by nine steps including "+4: very hot" and "−4: very cold" in addition to the seven steps illustrated in FIG. 4.

As illustrated in FIG. 3, the thermal sensation estimator 108 includes a camera 103, a globe thermometer 104a, a thermometer 104b, an anemometer 105a disposed in the vicinity of a louver 105b, a hygrometer 107, and a thermal-sensation estimation controller 106 connected to these elements.

The thermal sensation estimator 108 is a processor that obtains a thermal sensation index obtained by indexing, in a specified range, an estimated thermal sensation of the person 102. The thermal sensation estimator 108 obtains, specifically, a thermal sensation index estimated based on the PMV. In this case, the specified range is represented by a seven-step evaluation scale for the PMV, and a predetermined range described below is a range in which the PMV value is −2 or more and is +2 or less in the seven steps. Although the following description will be given of an example in which the thermal sensation estimator 108 obtains the thermal sensation index by estimating it, the thermal sensation estimator 108 may also obtain a thermal sensation index estimated by another device or the like and transmitted therefrom.

The configuration of the thermal sensation estimator 108 will now be described with reference to FIG. 5.

The air temperature of the six thermal factors can be obtained from the thermometer 104b.

The radiant temperature of the six thermal factors can be obtained from the globe thermometer 104a and the thermometer 104b. The globe thermometer has a structure in which a glass thermometer is inserted into a black-colored, copper ball. Since the globe thermometer measures not only an ambient air temperature but also a temperature including an ambient radiant temperature by using the copper ball painted with black, it is possible to assess the influence of the radiant temperature, depending on a difference between a measurement value of the globe thermometer 104a and a measurement value of the thermometer 104b.

The air speed of the six thermal factors is measured by an anemometer 105. The anemometer 105 corresponds to the above-described anemometer 105a.

The humidity of the six thermal factors is measured by the hygrometer 107.

The amount of clothing of the six thermal factors can be obtained by analyzing an image of the person 102 which is captured by the camera 103. That is, an amount-of-clothing estimator 106a in the thermal-sensation estimation controller 106 obtains the amount of clothing by performing calculation on an image of the person 102 which is captured by the camera 103. On the basis of an image captured by the camera 103, the amount-of-clothing estimator 106a may obtain the amount of clothing, for example, by determining the area of a clothing part and the area of an exposed part, that is, a skin part, and using the ratio of the clothing-less part of the person 102 to the clothing part or using the ratio of a wrist, which is an exposed part, to an arm portion, which is a clothing part, or by using a temperature difference between a clothing part and an exposed part. This is because the temperature of a clothing surface tends to get closer to the body surface temperature as the amount of clothing decreases. Naturally, the amount of clothing may be determined by another means or may be reported by the person 102.

The amount of human activity of the six thermal factors when driving a vehicle is close to that in an almost sedentary state, and is generally thought to be about 1.1 METs (the metabolic equivalent of task) without particular measurement. Even when the human-state estimating device is used in a place other than in a vehicle, for example, it is possible to estimate the amount of activity by capturing moving images of the person 102 with the camera 103, locating a human region in each image of the moving images, and using the amount of change of the human region.

With the above-described scheme, it is possible to extract the six thermal factors for the person 102. The six-thermal-factor determination method described above is merely an example and is not limiting.

Next, the amount of clothing determined by the amount-of-clothing estimator 106a, the temperature and the radiant temperature determined by the globe thermometer 104a and the thermometer 104b, the air speed determined by the anemometer 105, and the humidity determined by the hygrometer 107 are input to a PMV calculator 106b in the thermal-sensation estimation controller 106, and the PMV calculator 106b calculates the thermal sensation of the person 102 in accordance with a PMV calculation expression. The description thus far has been given of how the thermal sensation estimator 108 operates.

Next, a method for estimating the human state estimation by using a nasal skin temperature will be described by way of example.

Figure 6:
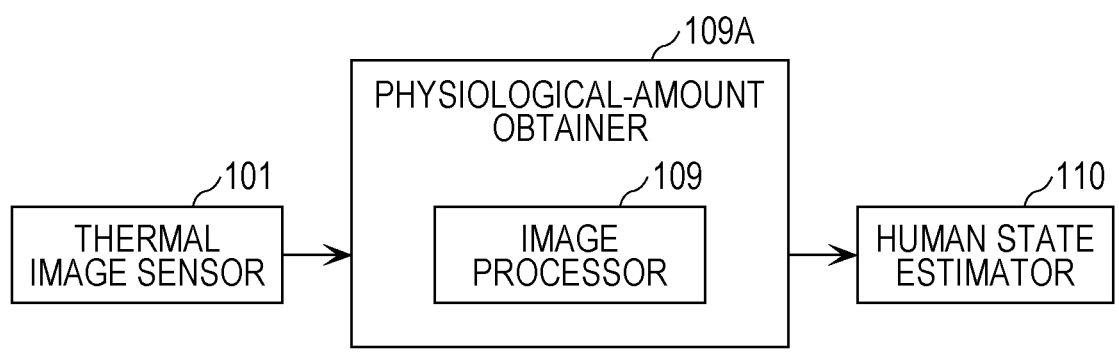
FIG. 6 is a block diagram illustrating functions for human state estimation in the first embodiment.

FIG. 6 is a block diagram illustrating functions for human state estimation in the present embodiment.

These functions are realized by the thermal image sensor 101, a physiological-amount obtainer 109A, and a human state estimator 110.

The thermal image sensor 101 acquires a thermal image of the person 102.

The physiological-amount obtainer 109A is a processor that obtains a physiological amount from the thermal image acquired by the thermal image sensor 101. The physiological-amount obtainer 109A has an image processor 109 and uses the image processor 109 to obtain the physiological amount. A description is this case is given of an example in which the skin temperature of the nasal part of the person 102 is used as the physiological amount.

The image processor 109 extracts the nasal part from the thermal image of the person 102 acquired by the thermal image sensor 101 and determines a nasal skin temperature, which is the temperature of the extracted nasal part. A method for extracting the nasal skin temperature is described later in conjunction with an example thereof. The physiological-amount obtainer 109A inputs the nasal skin temperature determined by the image processor 109 to the human state estimator 110, and the human state estimator 110 estimates the human state on the basis of the nasal skin temperature.

A description will be given of an example of processing when the human state estimator 110 senses the degree of sleepiness as the human state.

Figure 7A:
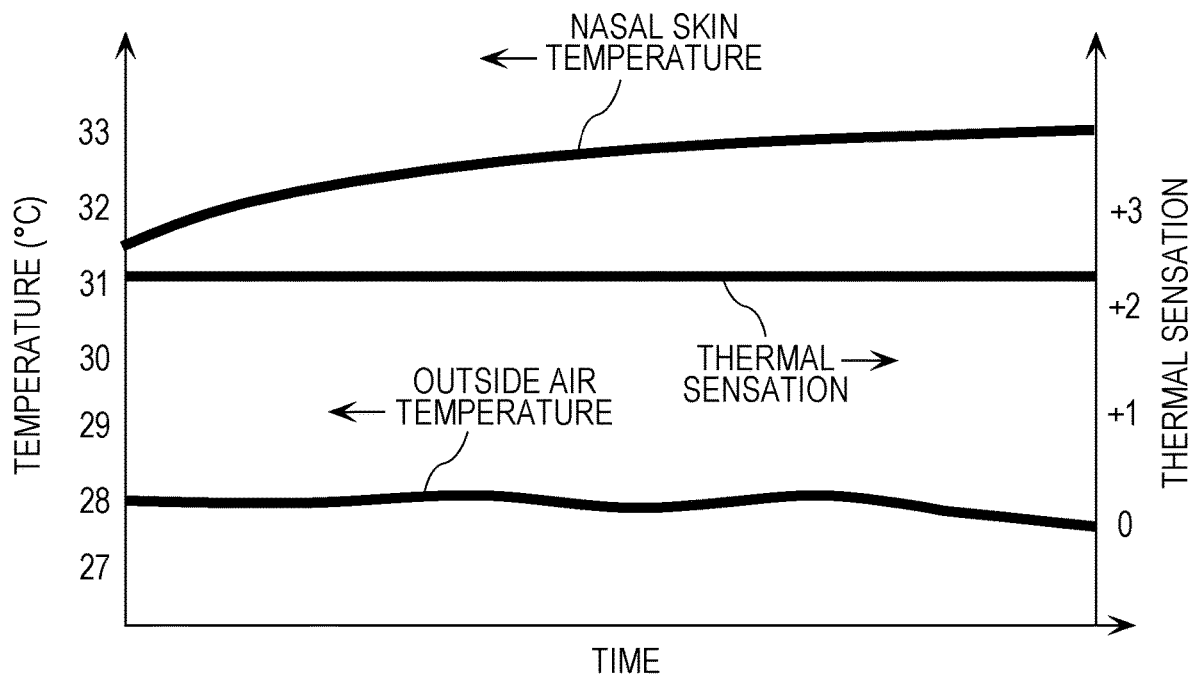
FIG. 7A is a graph illustrating, in the first embodiment, an example of a case in which the thermal sensation is 2 or more and an outside air temperature and a nasal skin temperature fluctuate over time.

FIG. 7A is a graph illustrating, in the present embodiment, an example of a case in which the thermal sensation is 2 or more and an outside air temperature and a nasal skin temperature fluctuate over time.

FIG. 7A illustrates transitions of the nasal skin temperature determined by the physiological-amount obtainer 109A, an ambient air temperature (an outside air temperature) of the person 102 which is measured by the thermometer 104b, and a thermal sensation of the person 102 which is determined by the thermal-sensation estimation controller 106 (the PMV calculator 106b). As illustrated in FIG. 7A, it is assumed that the outside air temperature is almost constant at about 28° C., and the thermal sensation exceeds +2. It is further assumed that the nasal skin temperature increases by about 1.5° C. in the illustrated time range.

When the human feels warm, the brain tries to promote blood flow by expanding the blood vessels of the peripheral parts in order to promote heat release from the body. As a result, the peripheral skin temperature increases. However, since the brain similarly tries to promote blood flow by expanding the peripheral blood vessels when the human feels sleepiness, as described above, it is difficult to determine whether the increase in the nasal skin temperature is due only to feeling hot or due also to feeling sleepy.

Figure 7B:
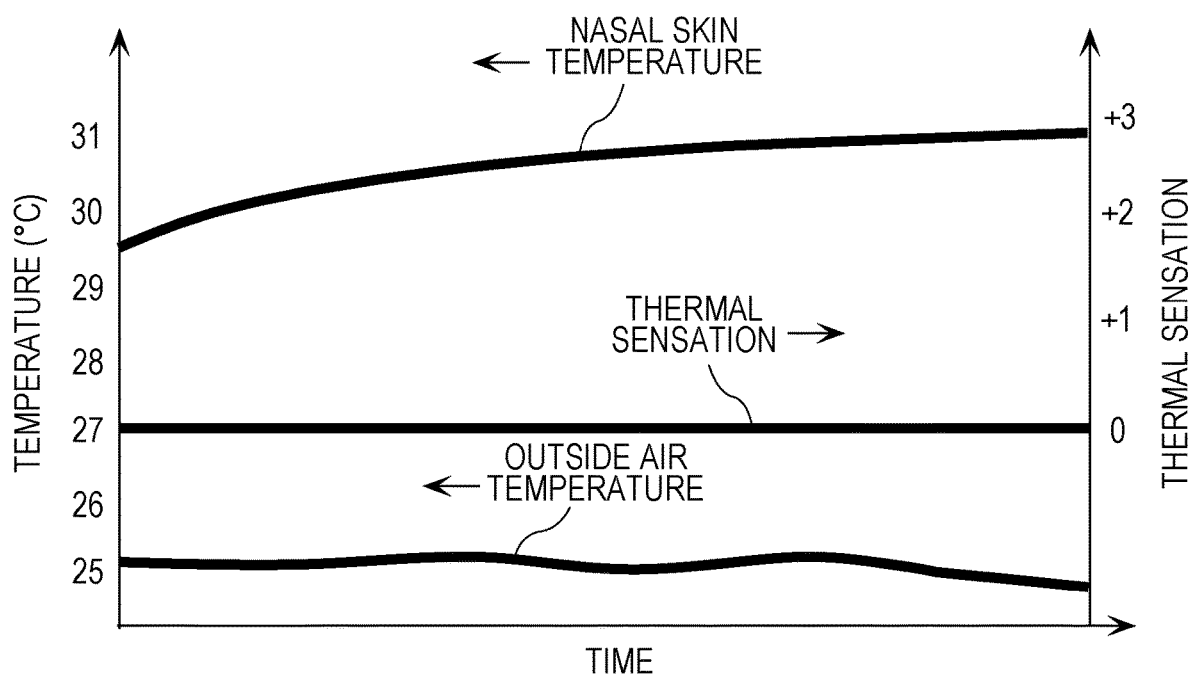
FIG. 7B is a graph illustrating, in the first embodiment, an example of a case in which the thermal sensation is equal or close to 0 and the outside air temperature and the nasal skin temperature fluctuate over time.

FIG. 7B is a graph illustrating, in the present embodiment, an example of a case in which the thermal sensation is equal or close to 0 and the outside air temperature and the nasal skin temperature fluctuate over time.

For example, as illustrated in FIG. 7B, it is assumed that the outside air temperature decreases to about 25° C., which is lower than about 28° C. in the case in FIG. 7A, and the thermal sensation is equal or close to zero, which is a thermoneutral point. It is also assumed that the nasal skin temperature increases by about 1.5° C. in the illustrated time range, as in the case in FIG. 7A (but the temperature differs from that in FIG. 7A).

In this case, since it is not necessary to promote heat release from the body, an increase in the skin temperature of a peripheral part, such as the nasal part, the increasing being caused by an increase in the blood flow rate of the peripheral part, is not observed. Hence, at a stage at which the thermal sensation is equal or close to the thermoneutral point, as illustrated in FIG. 7B, it is possible to assume that an increase in the nasal skin temperature, like that illustrated in FIG. 7B, is due to sleepiness.

In this case, it is difficult to estimate the thermal sensation, depending on in which temperature range the outside air temperature is. More specifically, for example, since the human thermal sensation differs depending on a difference in the amount of clothing (e.g., a case in which only a T-shirt is worn or a case in which warm clothes, such as a down jacket, are worn) even for the same outside air temperature, it is difficult to estimate the thermal sensation, depending on in which temperature range the outside air temperature is. Hence, it is important to make a determination based on the human thermal sensation, not merely on the outside air temperature.

The degree of sleepiness may be divided into five steps depending on the temperature range in which the nasal skin temperature fluctuates, as illustrated in FIG. 8. When the fluctuation range of the nasal skin temperature is large, it can be determined that the person is very sleepy. Also, a stage at which the fluctuation range of the nasal skin temperature is small may be regarded as a stage at which the person is slightly sleepy, and the relationship between the fluctuation range of the nasal skin temperature and the degree of sleepiness may be determined depending on a difference in the fluctuation range of the temperature, as appropriate.

Next, a description will be given of one example of processing when the human state estimator 110 senses a degree of stress as the human state.

Figure 9A:
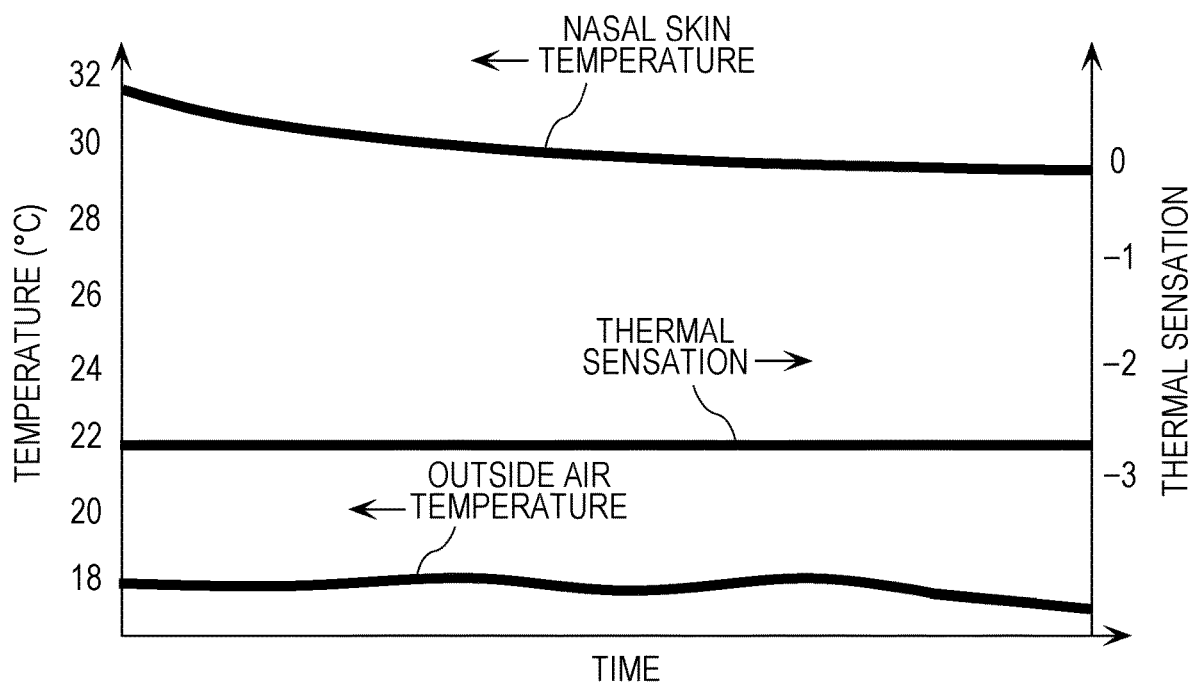
FIG. 9A is a graph illustrating, in the first embodiment, an example of a case in which the thermal sensation is −2 or less and the outside air temperature and the nasal skin temperature fluctuate with time.

FIG. 9A is a graph illustrating, in the present embodiment, an example of a case in which the thermal sensation is −2 or less and the outside air temperature and the nasal skin temperature fluctuate with time.

FIG. 9A illustrates transitions of the nasal skin temperature determined by the physiological-amount obtainer 109A, an ambient air temperature (an outside air temperature) of the person 102 which is measured by the thermometer 104b, and a thermal sensation of the person 102 which is determined by the thermal-sensation estimation controller 106 (the PMV calculator 106b). It is now assumed that the outside air temperature is almost constant at about 18° C., and the thermal sensation falls below −2, as illustrated in FIG. 9A. When the human feels cold, the brain tries to reduce blood flow by constricting blood vessels of peripheral parts in order to suppress heat release from the body. Hence, the skin temperatures of the peripheral parts decreases. However, when the human feels stress, the brain similarly tries to reduce the blood flow rate by constricting the peripheral blood vessels, as described above, and thus it is difficult to determine whether the decrease in the nasal skin temperature is due only to feeling cold or due also to feeling stress.

Figure 9B:
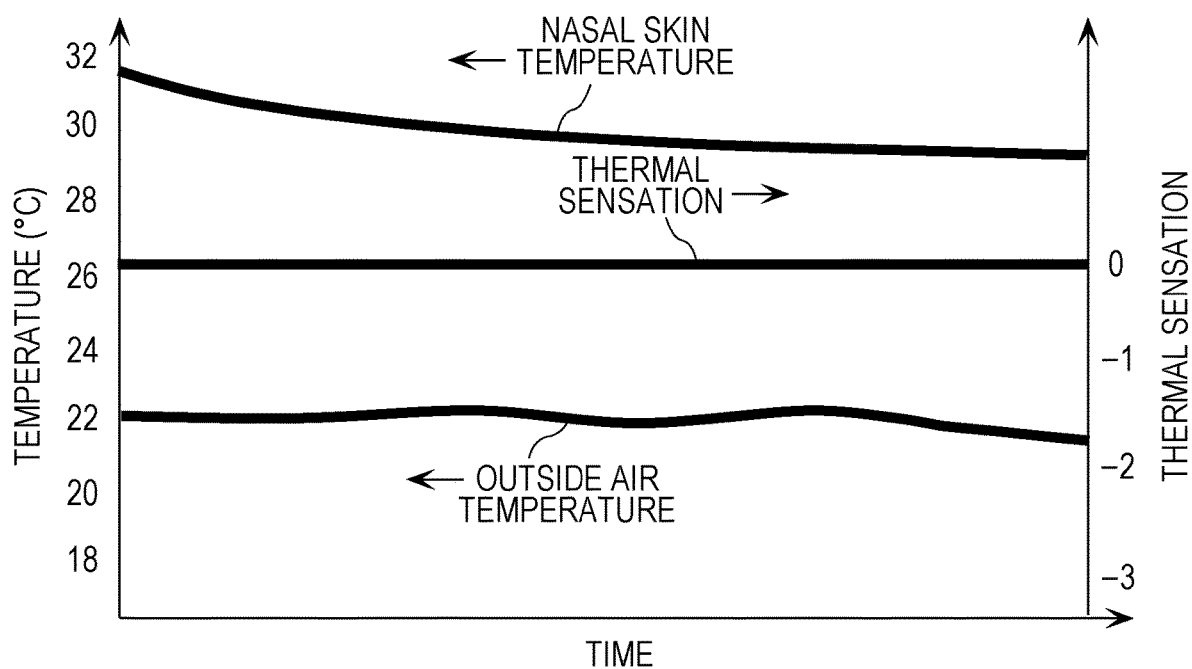
FIG. 9B is a graph illustrating, in the first embodiment, an example of a case in which the thermal sensation is equal or close to 0 and the outside air temperature and the nasal skin temperature fluctuate over time.

FIG. 9B is a graph illustrating, in the present embodiment, an example of a case in which the thermal sensation is equal or close to 0 and the outside air temperature and the nasal skin temperature fluctuate over time.

For example, when the outside air temperature increases to about 22° C., which is higher than about 18° C. in the case in FIG. 9A, and the thermal sensation is equal or close to zero, which is the thermoneutral point, as illustrated in FIG. 9B, it is not necessary to suppress heat release from the body, and thus, a decrease in the skin temperature of a peripheral part, such as the nasal part, the decrease being caused by a decrease in the blood flow rate of the peripheral part, is not observed. Hence, at a stage at which the thermal sensation is equal or close to the thermoneutral point, as illustrated in FIG. 9B, it is possible to assume that a decrease in the nasal skin temperature, like that illustrated in FIG. 9B, is due to stress.

In this case, it is difficult to estimate the thermal sensation, depending on in which temperature range the outside air temperature is. More specifically, for example, since the human thermal sensation differs depending on a difference in the amount of clothing (e.g., a case in which only a T-shirt is worn or a case in which warm clothes, such as a down jacket, are worn) even for the same outside air temperature, it is difficult to estimate the thermal sensation, depending on in which temperature range the outside air temperature is. Hence, it is important to make a determination based on the human thermal sensation, not merely on the outside air temperature.

The degree of stress may be divided into a plurality of steps according to the range in which the nasal skin temperature fluctuates, as in the case of the degree of sleepiness illustrated in FIG. 8. When the fluctuation range of the nasal skin temperature is large, it is possible to determine that the person is feeling strong stress. Also, a stage at which the fluctuation range of the nasal skin temperature is small may be regarded as a stage at which the person is feeling mild stress, and the relationship between the fluctuation range of the nasal skin temperature and the degree of stress may be determined depending on a difference in the fluctuation range of the temperature, as appropriate.

Next, a description will be given of the configuration of a human-state estimating device 113 in the present embodiment.

Figure 10:
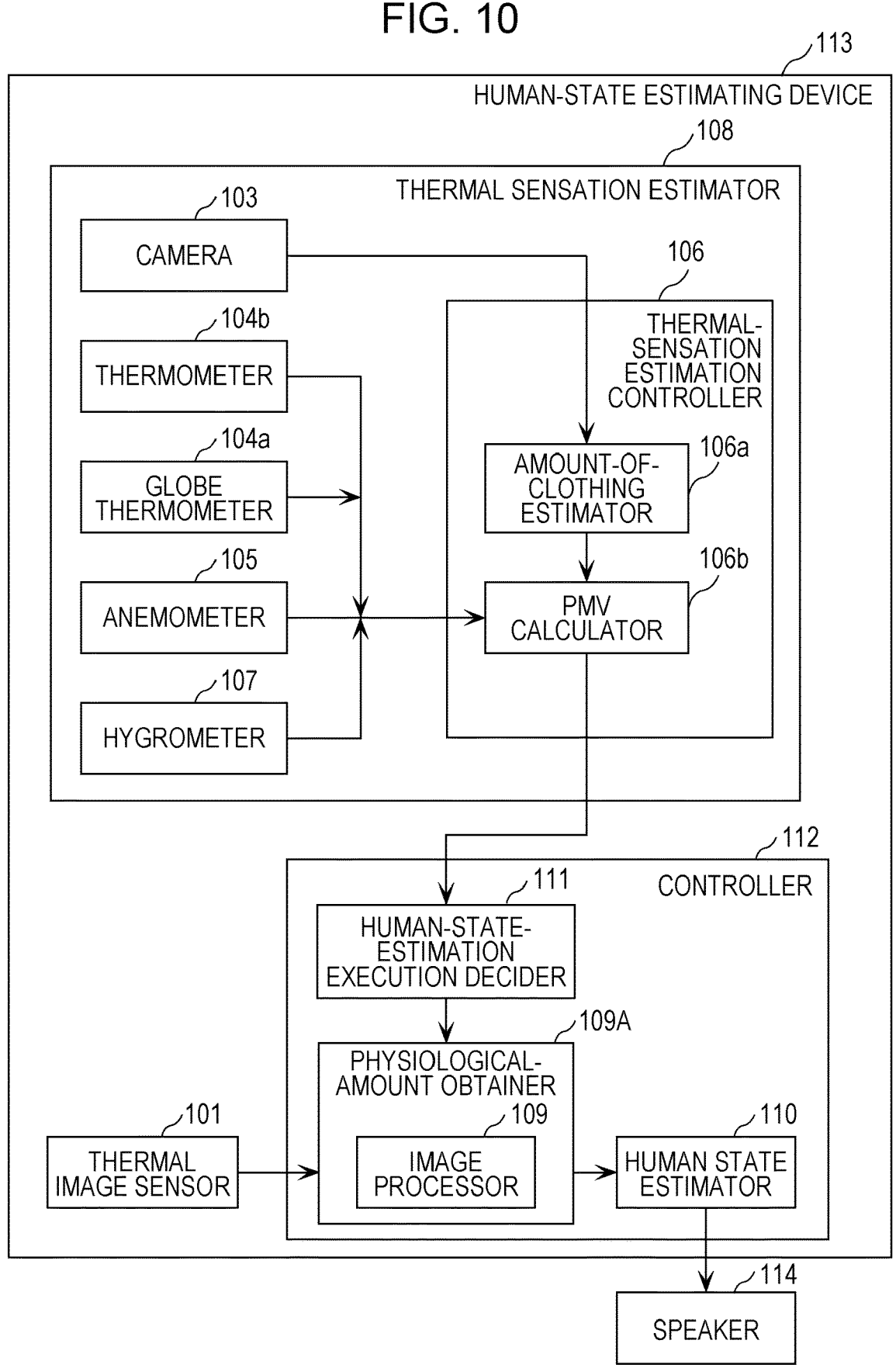
FIG. 10 is a block diagram illustrating the function of the human-state estimating device in the first embodiment.

FIG. 10 is a block diagram illustrating the function of the human-state estimating device 113 in the present embodiment. The human-state estimating device 113 can also be called a human-state estimating system.

The human-state estimating device 113 includes a thermal sensation estimator 108, a thermal image sensor 101, and a controller 112. The human-state estimating device 113 is connected to a speaker 114.

Since the thermal sensation estimator 108 and the thermal image sensor 101 are the same as or similar to the above-described corresponding functional blocks having the same names, descriptions thereof are not given hereinafter.

The controller 112 includes a physiological-amount obtainer 109A, a human state estimator 110, and a human-state-estimation execution decider 111.

The physiological-amount obtainer 109A is a processor that obtains a physiological amount in which the activity of the human autonomic nervous system is reflected, when it is determined that the thermal sensation index obtained by the thermal sensation estimator 108 is in the predetermined range. By using the image processor 109, the physiological-amount obtainer 109A processes the thermal image, obtained by the thermal image sensor 101, to obtain a nasal skin temperature as a physiological amount.

The human state estimator 110 is a processor that estimates the human state on the basis of the physiological amount obtained by the physiological-amount obtainer 109A. More specifically, the human state estimator 110 is a processor that estimates the degree of stress or sleepiness, which is a human state, on the basis of the nasal skin temperature determined by the physiological-amount obtainer 109A.

The human-state-estimation execution decider 111 is a processor that determines whether or not the thermal sensation index obtained by the thermal sensation estimator 108 is in the predetermined range in the specified range. The result of the determination is used for the human state estimator 110 to decide whether or not to execute estimation of the human state. The human-state-estimation execution decider 111 is connected to the thermal-sensation estimation controller 106 (the PMV calculator 106b) in the thermal sensation estimator 108. A result of the estimation of the thermal sensation of the person 102 is input to the human-state-estimation execution decider 111. The human-state-estimation execution decider 111 is connected to the physiological-amount obtainer 109A. The human-state-estimation execution decider 111 corresponds to a determiner.

The human-state-estimation execution decider 111 may also be connected to the human state estimator 110. In this case, the human-state-estimation execution decider 111 does not necessarily have to be connected to the physiological-amount obtainer 109A. In this case (i.e., in a case in which the human-state-estimation execution decider 111 is not connected to the physiological-amount obtainer 109A and is connected to the human state estimator 110), the physiological-amount obtainer 109A always preforms processing for obtaining a human physiological amount. The human state estimator 110 estimates the human state by using a physiological amount that the physiological-amount obtainer 109A obtains at a timing when the human-state-estimation execution decider 111 determines that the thermal sensation index obtained by the thermal sensation estimator 108 is in the predetermined range in the specified range. That is, the human state estimator 110 does not use, for estimating the human state, a physiological amount that the physiological-amount obtainer 109A obtains at a timing when the human-state-estimation execution decider 111 determines that the thermal sensation index obtained by the thermal sensation estimator 108 is not in the predetermined range in the specified range.

The speaker 114 is an output device that alerts the person 102 in accordance with a result of the human state estimation performed by the human state estimator 110. The speaker 114 may be a portion of the human-state estimating device 113.

The human-state estimating device 113 may be implemented as a single device in which the above-described functional blocks are housed in one housing or may be implemented by an architecture in which the above-described functional blocks are arranged in a distributed manner to transmit/receive information through a communication channel.

Now, a description will be given of a flow of processing performed by the human-state estimating device 113.

Figure 11:
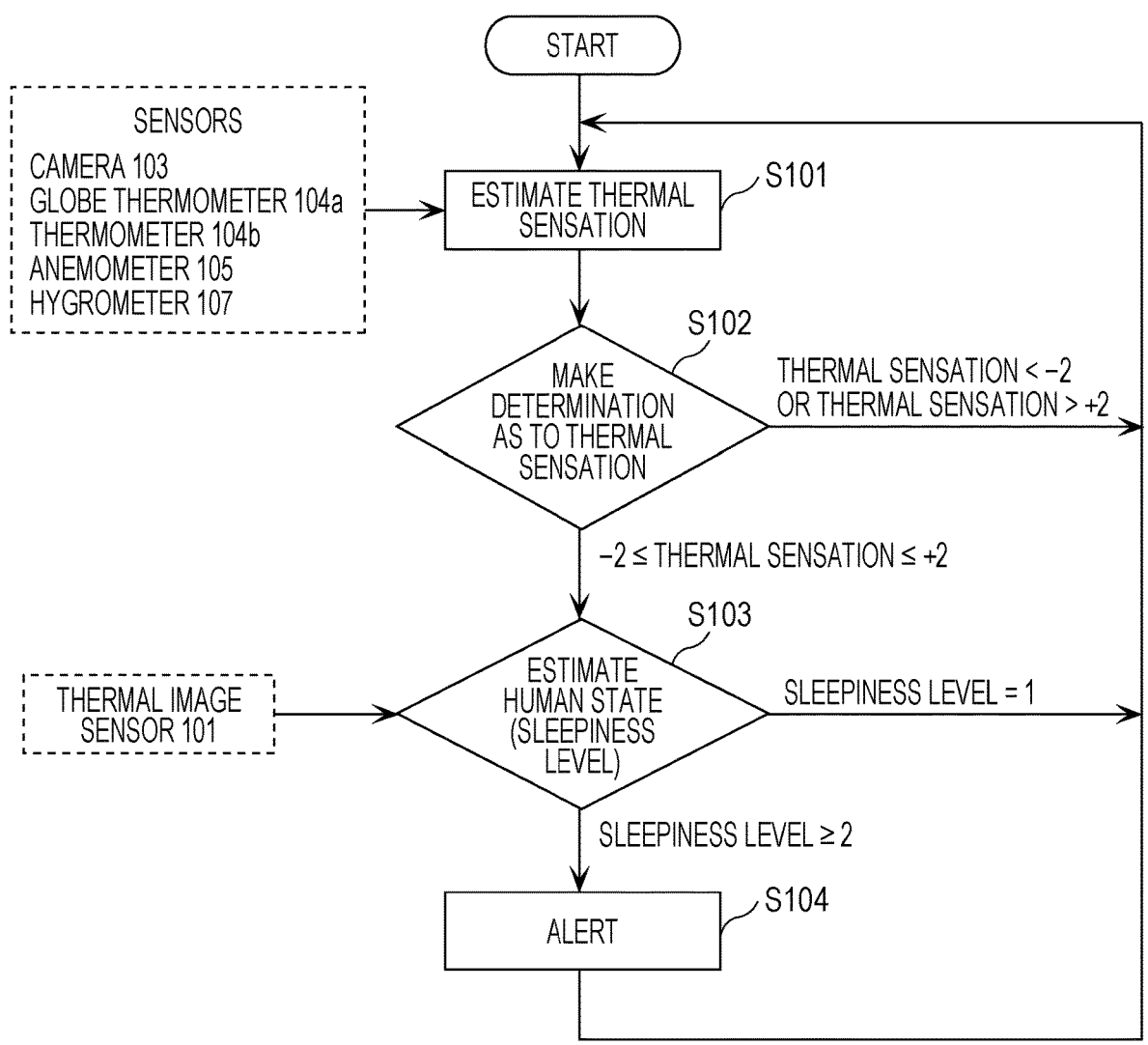
FIG. 11 is a flow diagram illustrating a method for human state estimation performed by the human-state estimating device in the first embodiment.

FIG. 11 is a flow diagram illustrating a method for human state estimation performed by the human-state estimating device 113 in the present embodiment.

In step S101, data obtained by the individual sensors (the camera 103, the globe thermometer 104a, the thermometer 104b, the anemometer 105, and the hygrometer 107) are input to the PMV calculator 106b, which estimates the thermal sensation of the person 102.

In step S102, the thermal sensation of the person 102 which was estimated in step S101 is input to the human-state-estimation execution decider 111, and the human-state-estimation execution decider 111 makes a determination as to the thermal sensation. More specifically, the human-state-estimation execution decider 111 determines whether or not the thermal sensation is in the predetermined range. The predetermined range can be set to, for example, a range in which the thermal sensation is −2 or more and +2 or less. The predetermined range may be a partial range of the specified range, the partial range including a thermoneutral point for thermal sensation. The predetermined range may be a partial range of the specified range, the partial range not including a point indicating being hottest as the thermal sensation and a point indicating being coldest as the thermal sensation.

If it is determined in step S102 that the thermal sensation is less than −2 or is more than +2, the process returns to step S101, and the PMV calculator 106b estimates the thermal sensation of the person 102 again. In this case, processes in steps S103 and S104 described below are not performed. If it is determined that the thermal sensation is less than −2 or is more than +2, the human state estimator 110 may estimate that the sleepiness level is 1, since it is known that the human whose thermal sensation is "very cold" or "very hot" is less likely to feel sleepy.

If it is determined in step S102 that the thermal sensation is in the range that is −2 or more and is +2 or less, the process proceeds to step S103.

In step S103, the human state estimator 110 estimates the sleepiness level as a human state, based on the nasal skin temperature that the physiological-amount obtainer 109A obtained based on the thermal image acquired by the thermal image sensor 101. More specifically, the human state estimator 110 estimates the degree of sleepiness of the person 102, based on the range of an increase in the nasal skin temperature over time. For example, when the nasal skin temperature increases by 1° C. in the time range in which the nasal skin temperature is measured (e.g., a time range indicated by the horizontal axis illustrated in FIG. 7A and so on), the human state estimator 110 determines that the sleepiness level is 2. When the nasal skin temperature increases by 2° C. in the time range, the human state estimator 110 determines that the sleepiness level is 4.

Also, a determination is made as to the estimated sleepiness level, and processing is performed in accordance with a result of the determination, as described below.

That is, if it is determined in step S103 that the sleepiness level is 1, the process returns to step S101 and then the series of processes illustrated in this flow diagram is performed. In this case, since the sleepiness level is a level that does not affect driving the vehicle by the person 102, for example, it is thought that the person 102 does not need to be alerted.

On the other hand, if it is determined in step S103 that the sleepiness level is 2 or more, the person 102 is alerted. In this case, since it is thought that the sleepiness level is a level that affects driving the vehicle by the person 102, the alerting is performed in order to notify the person 102 about it. The alerting involves, for example, notifying the person 102 that the he or she is getting sleepy, urging the person 102 to take a rest, or the like by using the speaker 114. After the alerting, the process returns to step S101, and the series of processes illustrated in this flow diagram is performed again.

When the degree of stress is estimated as the human state, the human state estimator 110 performs a different process in step S103. Specifically, the human state estimator 110 estimates the degree of stress as the human state, based on the nasal skin temperature that the physiological-amount obtainer 109A obtained based on the thermal image acquired by the thermal image sensor 101. More specifically, the human state estimator 110 estimates the degree of stress of the person 102, based on the range of a decrease in the nasal skin temperature over time. Other processes are substantially the same as those described above.

Thus, it is possible to determine whether a variation in the skin temperature is due to the human thermal sensation or due to sleepiness, thus making it possible to provide a high-accuracy degree-of-sleepiness estimating means. Naturally, the same applies to the degree of stress, which is a human state, and similarly, it is possible to provide a high-accuracy degree-of-stress estimating means. Thus, it is possible to provide a high-accuracy human-state estimating means. Also, for detecting the degree of sleepiness, for example, when the thermal sensation is −2 or less or is +2 or more, that is, when the human feels cold or hold, the human is less likely to feel sleepy. This makes it possible to omit unwanted estimation of the degree of sleepiness, the estimation being performed by the controller 112, and offers advantages that the processing load can be reduced and the energy consumed can be reduced.

Although the above description has been given of an example in which the human state estimator 110 estimates the sleepiness, and the person 102 is notified via the speaker 114 when the resulting sleepiness level is 2 or more, the means for notifying the person 102 is not limited thereto. For example, the seat belt may be fastened tight to urge the user to be awake or a warning may be displayed on a display or the like to notify the person 102, and the method for the notification is not particularly limiting.

In addition, although a case in which the physiological-amount obtainer 109A (the image processor 109) determines the nasal skin temperature on the basis of the thermal image captured by the thermal image sensor 101 has been described above, the temperature determined by the physiological-amount obtainer 109A is not limited to the nasal skin temperature, and may be the temperature of any similar part corresponding to a peripheral part. Examples of such a part include the back of a hand or an earlobe of the person 102. However, when human state estimation is performed in the vehicle 100, a lower body part of the person 102 (in other words, a part closer to the feet) is more likely to be affected by insolation. Thus, it is desirable to use the skin temperature of a part above the neck, and measuring the temperature at the nasal part or the earlobe part makes it possible to perform human state estimation that is less susceptible to disturbance due to insolation.

In addition, although, in the human-state-estimation execution decider 111, the lower limit and the upper limit of the range of the thermal sensation determined by the PMV calculator 106b are −2 and +2, respectively, the lower and upper limits may be different from these values. For example, the human state may be estimated using a thermal sensation that is −1 or more and is +1 or less. When this range includes the thermoneutral point and is small, the human state can be estimated with higher accuracy. Naturally, for example, decimal numbers, such as −1.5 and +1.5, rather than integers may be used as thresholds.

Although the description thus far has been given of an example of a case in which the thermal sensation estimator 108 automatically estimates the human thermal sensation, for example, the person 102 may directly input the thermal sensation of the person 102. As long as a value that enables determination of the thermal sensation of the person 102 can be provided to the human-state-estimation execution decider 111, the means therefor is not limiting.

Figure 12A:
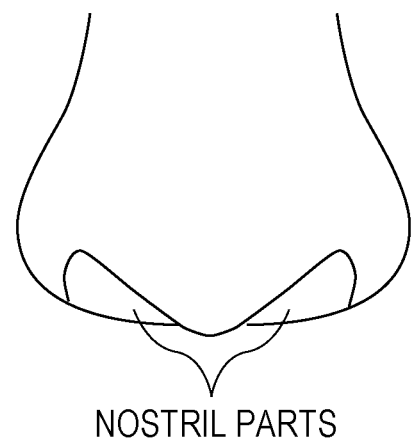
FIG. 12A is a schematic view for describing measuring a nasal skin temperature in the first embodiment.
Figure 12B:
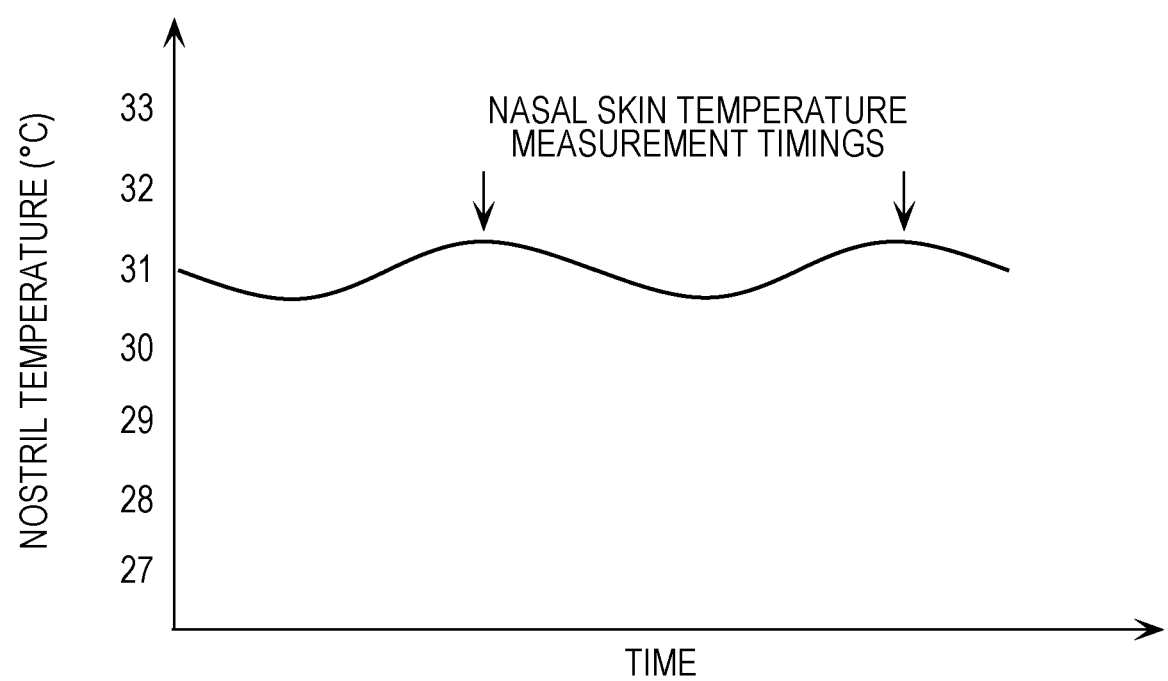
FIG. 12B is a graph illustrating fluctuations in a nostril part temperature during nasal-skin-temperature measurement in the first embodiment.

Also, when the physiological-amount obtainer 109A (the image processor 109) determines the nasal skin temperature, it is necessary to locate the nasal part by using the thermal image acquired by the thermal image sensor 101. One example of such a case will now be described. FIG. 12A is a schematic view for describing measuring a nasal skin temperature in the present embodiment. FIG. 12B is a graph illustrating fluctuations in a nostril part temperature during nasal-skin-temperature measurement in the present embodiment.

FIG. 12A is a schematic view of a human nose, and when the human take breaths, the temperature of the nostril parts fluctuates according to a respiration cycle as illustrated in FIG. 12B. This temperature fluctuation is due to a temperature increase caused by an increase in the temperature of the nostril parts when a breath warmed in the body is breathed out from the nose during respiration and due to a temperature decrease caused by deprivation of the heat of the nostril parts when the outside air is breathed in. Thus, the cycle of the temperature fluctuation is almost equal to a respiration cycle (typically, about 0.2 to 0.3 Hz). Hence, when the image processor 109 finds two parts whose temperatures fluctuate at a cycle of about 0.2 to 0.3 Hz, it assumes that the parts are nostril parts. When the nostril parts are found, the nasal part whose skin temperature is to be measured can be easily located based on the positions of the nostril parts. With the above-described scheme, it is possible to locate the nasal part.

When the nostril parts cannot be located, the person 102 may be notified via the display or the like that the nostril parts cannot be extracted and the human state cannot be estimated. At the same time, for example, the person 102 may be prompted so as to wear eyeglasses or the like. Eyeglasses generally do not allow infrared light to pass therethrough, and thus, when the thermal image sensor 101 captures an image of a person wearing eyeglasses, the portion corresponding to the eyeglasses represents the temperature of the eyeglasses, not the temperature of the eyes. Thus, the temperature of the eyeglasses is closer to the ambient temperature than to the skin temperature, thereby making it easier to detect the position of the nasal part. Estimating and measuring the position of the nasal part on the basis of the detected eye positions makes it possible to accurately estimate the position of the nasal part.

In addition, the person 102 may be prompted via the display or the like so as to take a deep breath. Deep breathing increases the amplitude of the nostril part temperature illustrated in FIG. 12B, thus making it easier to extract the positions of the nostril parts. Naturally, another method may be used to identify the nasal part. For example, the nasal part may be estimated by extracting a human's face and using the contour of the face, and a method for identifying the nasal part is not limiting.

Also, when the nasal skin temperature is measured for the human state estimation, the measurement timing thereof may be synchronized with the phase of respiration. For example, the nasal skin temperature may be measured at a timing when the temperature of the nostril parts is the highest each time respiration is performed, as indicated by arrows in FIG. 12B. Since the nostril part temperature is varied by respiration, the nasal skin temperature is also affected by the variation. Thus, measuring the nasal skin temperature in synchronization with the phase of the respiration makes it possible to perform fine measurement with fewer variations. Although an example in which the nostril part temperature is measured at the timing at which the temperature of the nostril parts is the highest each time respiration is performed has been described above, naturally, the measurement may be performed at another phase, for example, at a timing at which the nostril part temperature is the lowest, and the timing is not limiting in this case.

In addition, although a case in which the thermal image sensor 101 is used to measure the nasal skin temperature has been described above, the present disclosure is not intended to limit the means for the measurement. For example, any means that can measure the skin temperature may be used, and a pyroelectric sensor or a single infrared sensor (such as a bolometer sensor or a thermopile sensor) may be used.

The human state may also be determined based on a skin blood flow rate. A method for determining the human state by using a skin blood flow rate will be described below.

Since there is a correlation that the blood flow rate in peripheral parts (particularly, the nasal part and so on) increases as the sleepiness increases, which is a human state, it is possible to estimate the human state by using the skin blood flow rate on the basis of the correlation. Various methods are possible as a method for measuring the skin blood flow rate. One example is a method in which light with a particular wavelength (e.g., infrared light) is received by a camera and the skin blood flow rate is calculated based on the amount of hemoglobin measured based on the received light.

The human state may also be determined based on a blood pressure. A method for determining the human state by using a blood pressure is described later with reference to FIGS. 12C and 12D.

Since there is a correlation the blood flow rate decreases as the sleepiness, which is a human state, increases, it is possible to estimate the human state by using the skin blood flow rate on the basis of the correlation. The blood pressure may be continuously determined using a cuff or may be determined using a pulse-wave propagation time. The "pulse-wave propagation time" refers to a time until a blood flow from the heart reaches a certain end part.

The blood pressure and the pulse-wave propagation time have a correlation that the pulse-wave propagation time increases as the blood pressure decreases. Hence, based on the correlation, the human state can be estimated from the pulse-wave propagation time via the blood pressure.

Figure 12C:
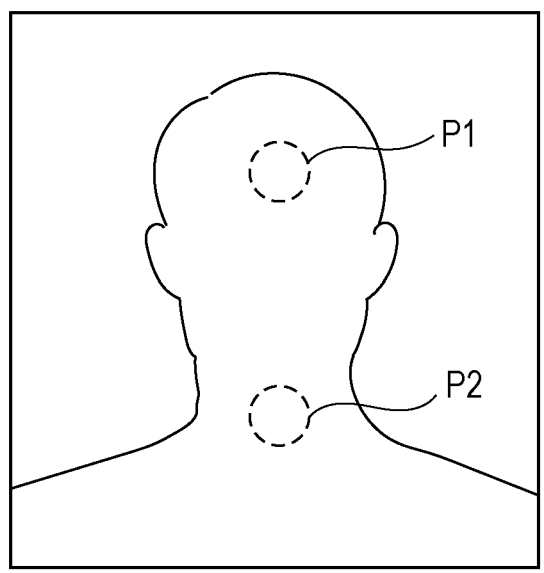
FIG. 12C is a schematic view illustrating a pulse-wave measuring method in the first embodiment.
Figure 12D:
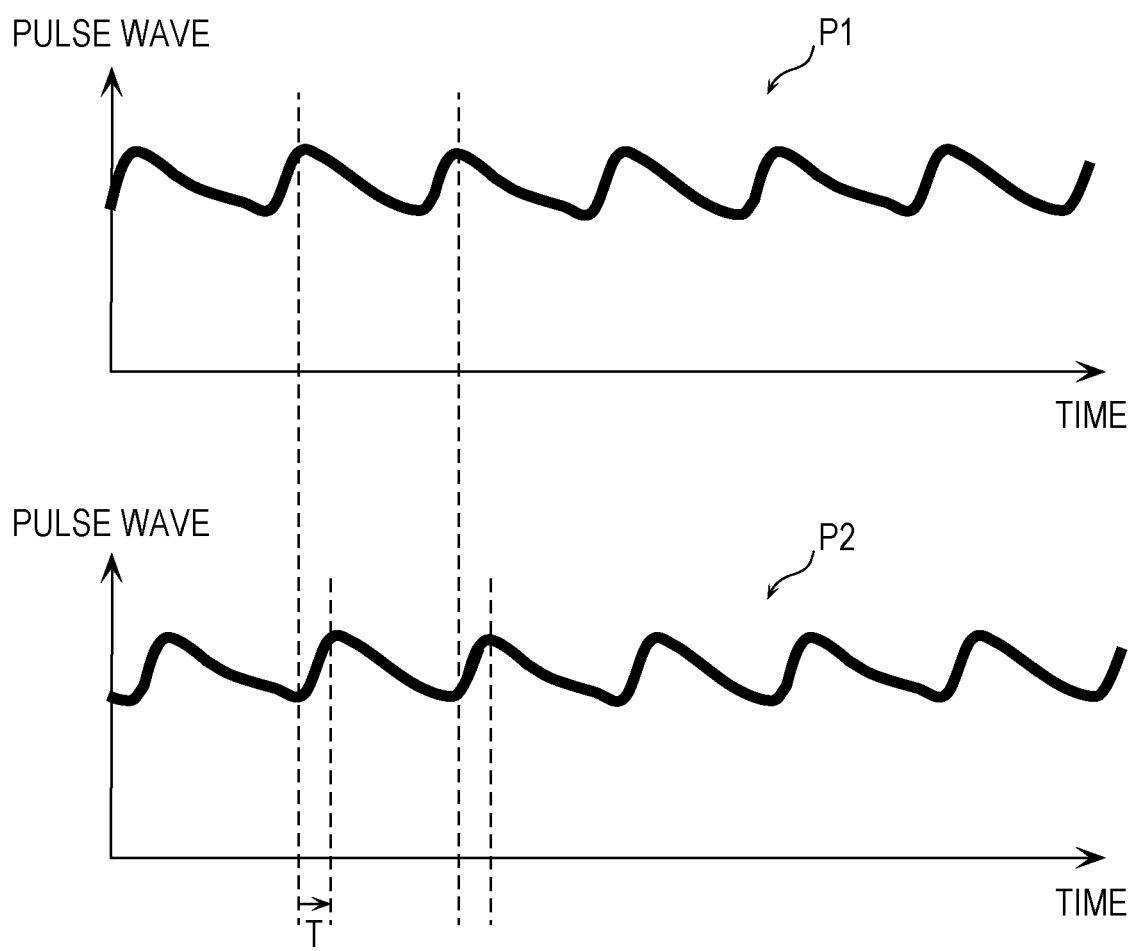
FIG. 12D is a schematic graph illustrating a pulse-wave measuring method in the first embodiment.

Various methods are possible as a method for measuring the pulse-wave propagation time. For example, moving images including a human face and a part P2 (such as the neck or a hand) other than the face, as illustrated in FIG. 12C, are captured using a camera, and a time difference T between the peak time of the pulse wave of a part P1 included in the face and the peak time of the pulse wave of the part P2 other than the face is determined based on the moving images, thereby making it possible to determine the pulse-wave propagation time (FIG. 12D). The time difference T is a value that can change in the range of about 0.2 ms variation.

The pulse-wave propagation time may also be determined using a time difference between the peak times of the pulse waves of two different parts (e.g., the jaw and the forehead) in the face, instead of using the face and a part other than the face. In addition, blood pressure variation may be estimated by measuring vibrations of the heart with a millimeter-wave sensor or the like, detecting the pulse wave of the face from a slight color variation in a face image captured by the camera, and using the amount of time difference between the vibration peak of the heart and the pulse wave peak of the face as the pulse-wave propagation time.

As described above, in the human-state estimating method according to the present embodiment, false detection during human state estimation is reduced to thereby make it possible to estimate the human state with higher accuracy. More specifically, in the human-state estimating method according to one aspect of the present disclosure, the human state is estimated based on a physiological amount under a situation in which the condition that the obtained thermal sensation information is in the predetermined range is satisfied. Thus, false detection during human state estimation can be reduced, compared with a case in which the human state is estimated regardless of whether or not the condition is satisfied. Accordingly, the above-described human-state estimating method makes it possible to improve the accuracy of estimating the human state. In addition, for example, a reduction of false detection eliminates the need for performing the detection processing again, thus offering advantages in that the throughput, the processing load, and the amount of power consumed decrease.

Also, when the human thermal sensation is in a range relatively close to a thermoneutral point at which the human feels neither hot nor cold, the human state is estimated. When the human feels hot or warm, the skin temperature increases through promotion of heat release from the body. In contrast, when the human feels cold or cool, the skin temperature decreases through suppression of heat release from the body. That is, when the human thermal sensation is in a range relatively close to the thermoneutral point, an influence of promotion or suppression of heat release from the human body is zero or relatively small. Hence, estimating the human state on the basis of the physiological amount in such a case can reduce the influence of promotion or suppression of heat release from the human body, the influence being included in the result of the estimation, and can contribute to preventing false detection and improving the estimation accuracy.

According to this arrangement, when the human thermal sensation is in a range excluding a case in which the human feels very hot or very cold, the human state is estimated. When the human feels very hot, the heat release from the human body is greatly promoted. Also, when the human feels very cold, the heat release from the human body is greatly suppressed. Excluding such cases from cases in which the human state is estimated can reduce the influence of promotion or suppression of the heat release from the human body, the influence being included in the result of the estimation, and can contribute to preventing false detection and improving the estimation accuracy.

When the degree of human sleepiness is estimated based on the human nasal skin temperature, it is possible to reduce the influence of promotion or suppression of heat release from his or her body, the influence being included in the result of the estimation. In addition, even when there is disturbance, use of the nasal skin temperature makes the estimation less susceptible to an influence of the disturbance.

Also, the degree of human sleepiness can be specifically estimated based on the human nasal skin temperature.

Since the estimation is performed based on the PMV, the human thermal sensation can be more accurately estimated based on an air temperature, a humidity, an air speed, a radiant temperature, the amount of clothing, and the amount of activity, which are six thermal factors.

The degree of human stress can be specifically estimated based on the human nasal skin temperature.

The degree of human sleepiness can be specifically estimated based on the human skin blood flow, blood pressure, or pulse-wave propagation time.

Second Embodiment

An example of a case in which a human-state estimating device in a second embodiment is provided in a vehicle will be described with reference to FIGS. 13A to 21.

Figure 13A:
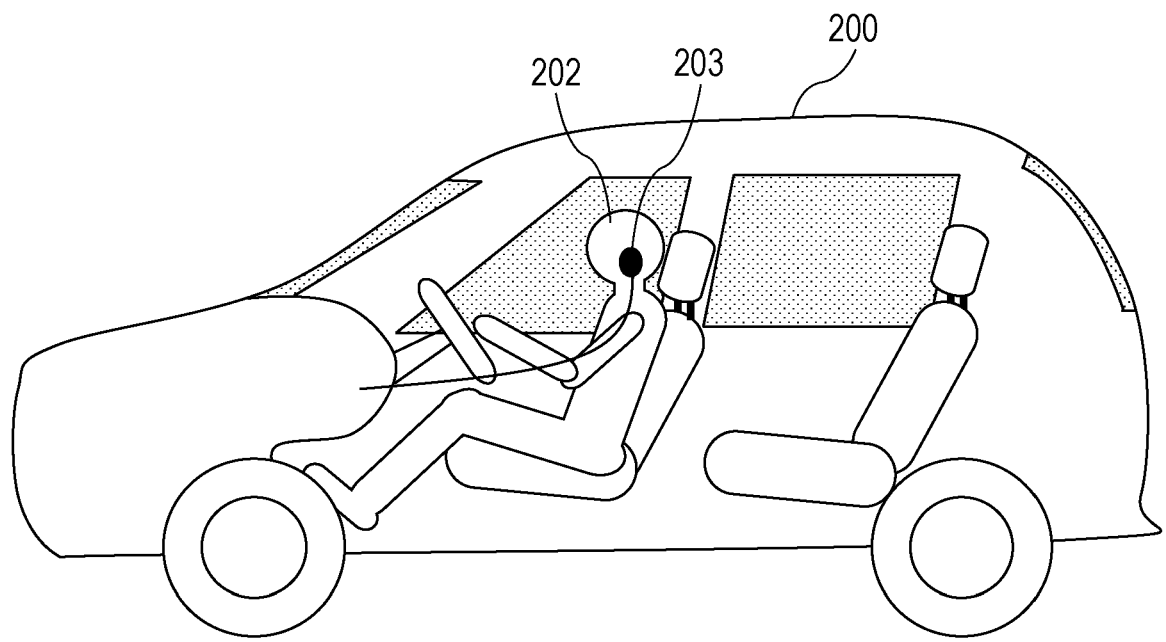
FIG. 13A is a conceptual diagram of a vehicle in which a human-state estimating device in a second embodiment is provided.
Figure 13B:
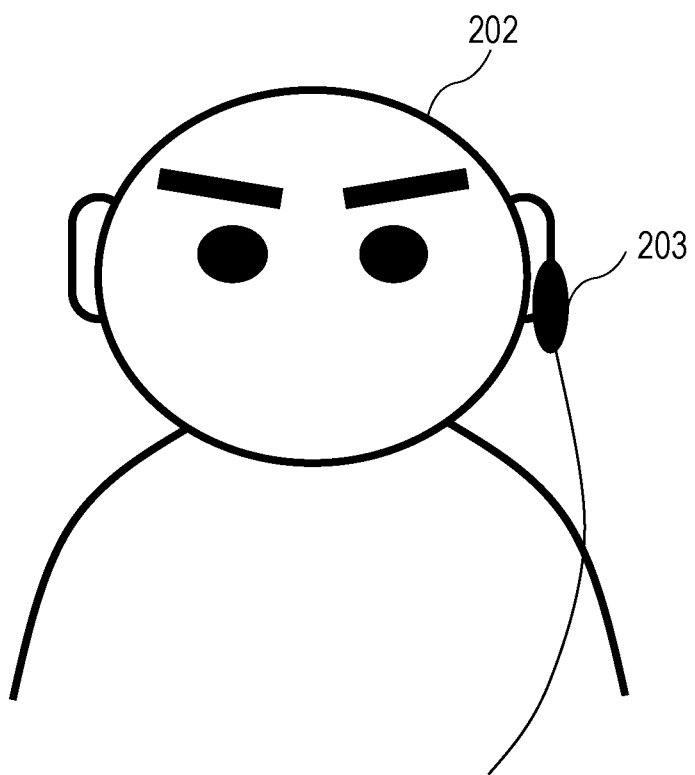
FIG. 13B is a schematic front view of a person wearing the human-state estimating device in the second embodiment.

FIG. 13A is a conceptual diagram of a vehicle 200 in which the human-state estimating device in the second embodiment is provided. FIG. 13B is a schematic front view of a person 202 wearing the human-state estimating device in the present embodiment. The person 202 illustrated in FIG. 13B corresponds to the person 202 who is in the vehicle 200 illustrated in FIG. 13A.

The person 202 wears a skin-temperature and pulse-wave sensor 203 on his or her earlobe part, as illustrated in FIG. 13B. The skin-temperature and pulse-wave sensor 203 is a sensor obtained by integrating a temperature sensor and a pulse wave sensor together and can measure a skin temperature and a pulse wave at the same time. In the present embodiment, a description will be given of an example in which the skin temperature of the earlobe part is used for thermal sensation estimation and a pulse wave is used for human state estimation.

The following description will be given of a method for human state estimation using a pulse wave.

Figure 14A:
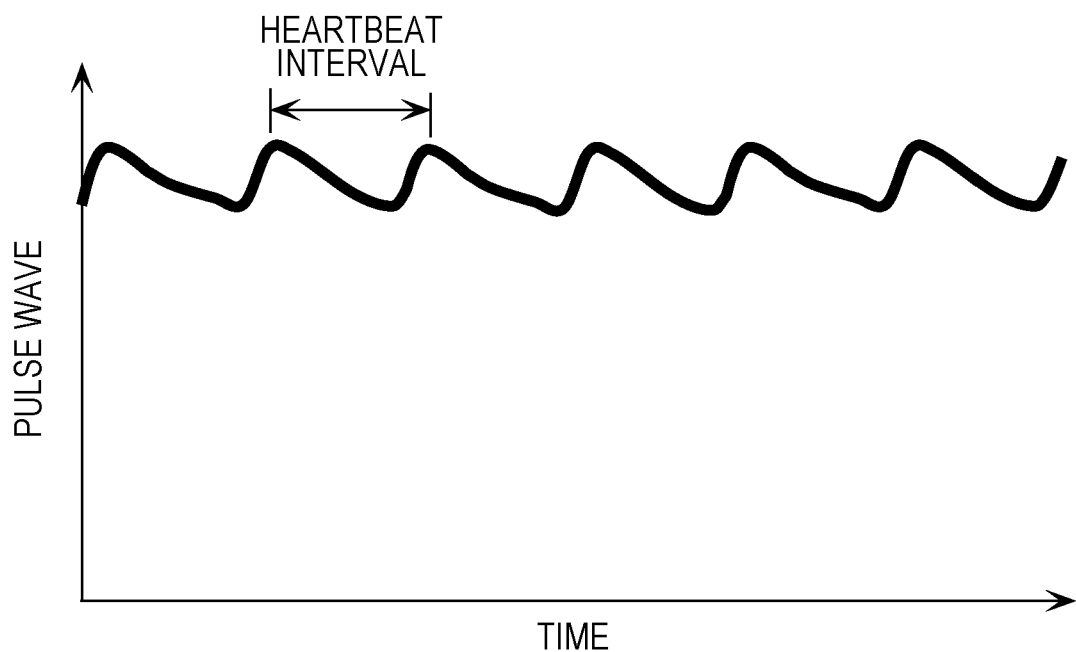
FIG. 14A is a graph illustrating one example of a pulse wave measured in the second embodiment.
Figure 14B:
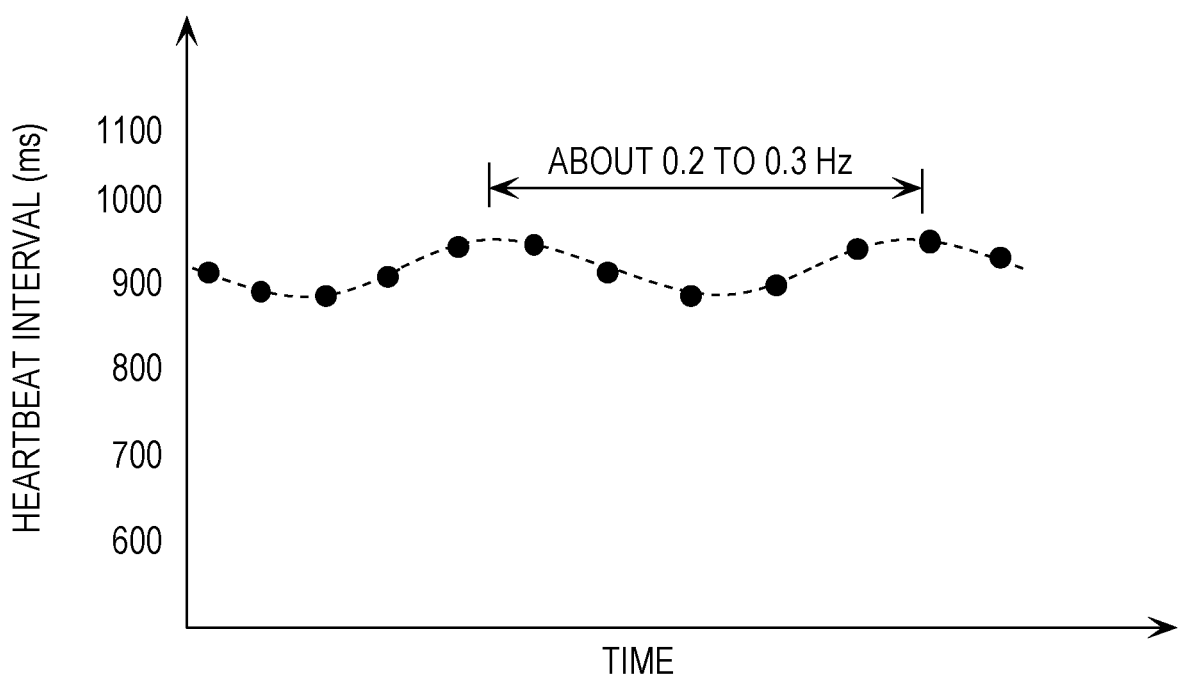
FIG. 14B is a graph illustrating variations in heartbeat intervals over time, the heartbeat intervals being obtained from the pulse wave illustrated in FIG. 14A.
Figure 15A:
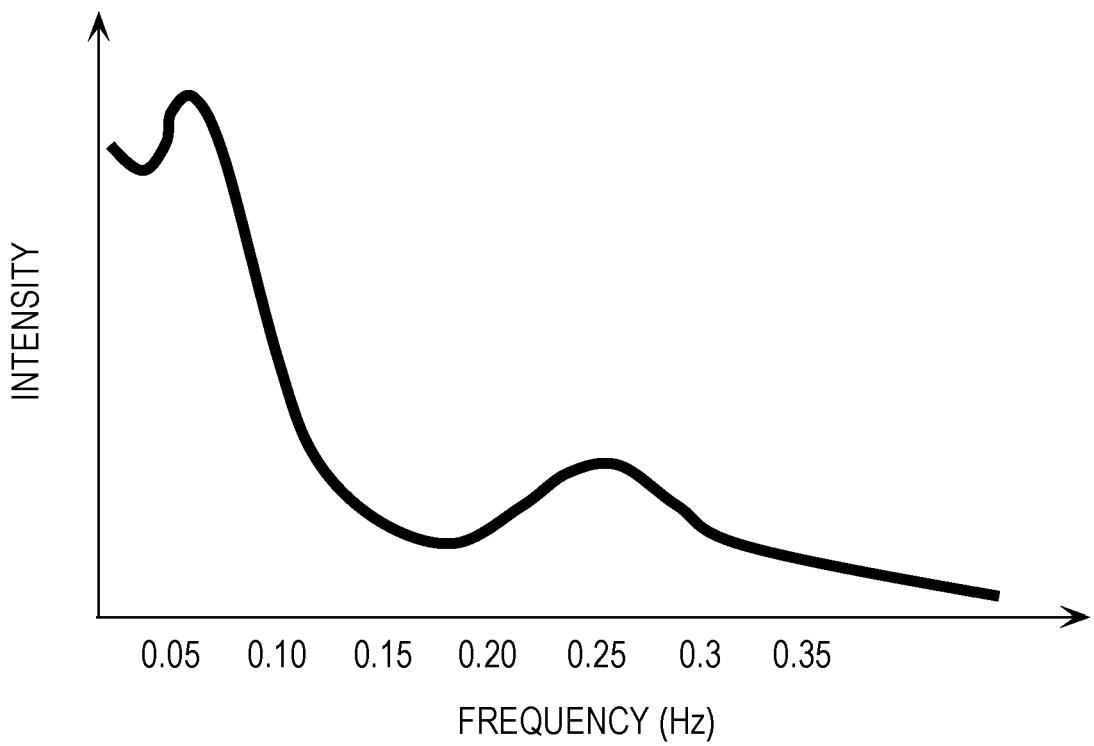
FIG. 15A is a graph illustrating frequency components of the heartbeat intervals in the second embodiment, the frequency components including a small amount of HF components.
Figure 15B:
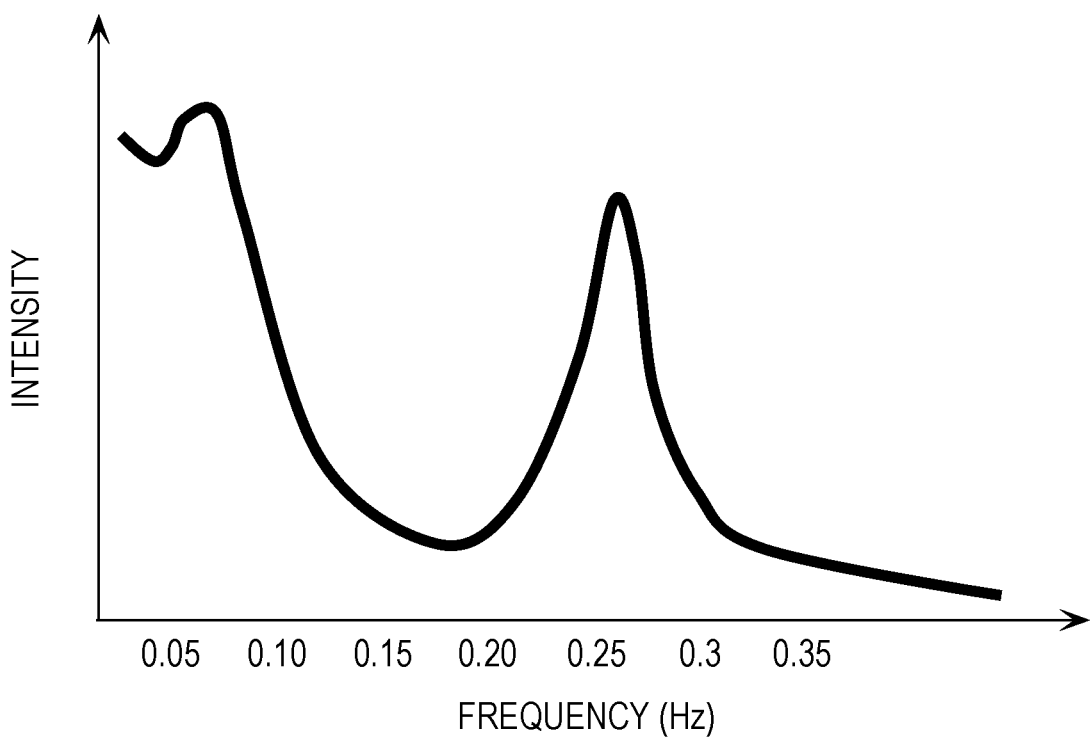
FIG. 15B is a graph illustrating frequency components of the heartbeat intervals in the second embodiment, the frequency components including a large amount of HF components.

FIG. 14A is a graph illustrating one example of a pulse wave measured in the present embodiment. FIG. 14B is a graph illustrating variations in heartbeat intervals over time, the heartbeat intervals being obtained from the pulse wave illustrated in FIG. 14A. FIG. 15A is a graph illustrating frequency components of the heartbeat intervals in the present embodiment, the frequency components including a small amount of HF components. FIG. 15B is a graph illustrating frequency components of the heartbeat intervals in the present embodiment, the frequency components including a large amount of HF components.

FIG. 14A is a graph illustrating one example of a pulse wave measured by the skin-temperature and pulse-wave sensor 203. The "pulse wave" is a wave obtained by regarding changes in the blood pressure or the blood volume in the peripheral blood vessel system, the changes being caused by heart beats, as a waveform from the body surface, and typically exhibits a sawtooth waveform, as illustrated in FIG. 14A. When the heartbeat intervals are extracted from the waveform of the pulse wave and are arranged in a time series, fluctuations in the heartbeat intervals (variations in the heartbeat intervals) over time are observed, as illustrated in FIG. 14B.

It is known that there are mainly two types of cause for the heartbeat interval fluctuation, one being variations in the blood pressure, and the other being a variation in the respiration. The heart beats are controlled by central neurons of the brain via the autonomic nervous system, constituted by two systems, that is, the sympathetic nervous system and the parasympathetic nervous system. For increasing the heart beats, the sympathetic nervous system increases its activity, and for reducing the heart beats, the parasympathetic nervous system increases its activity. The central neurons of the brain determine whether or not to increase or reduce the heart beats, on the basis of the state of the body, and factors for the determination include the blood pressure and the respiration. When the blood pressure decreases, the central neurons of the brain function so as to increase the heart beats in order to vitalize the activity of the heart, and when the blood pressure increases, the central neurons of the brain function so as to reduce the heart beats in order to reduce the activity of the heart. The respiration functions such that when the human takes a breath in as the lung expands, the heart beats increase, and when the human takes a breath out, the heart beats decrease.

Also, the blood pressure fluctuates at about 0.1 Hz, and this fluctuation is called Mayer waves. The respiration is about 0.2 to 0.3 Hz at rest. The heartbeat intervals exhibit a waveform having a cycle of 0.2 to 0.3 Hz or a waveform having a cycle of about 0.1 Hz, as illustrated in FIG. 14B.

Next, a description will be given of a speed (a response speed) at which the sympathetic nervous system and para- sympathetic nervous system respond to an instruction about the heartbeat speed, the instruction being given from the central neurons of the brain. It is known that the parasympathetic nervous system can respond to the instruction even when it has a fluctuation of about 0.2 to 0.3 Hz. On the other hand, it is known that the sympathetic nervous system can respond to the instruction when it has a fluctuation of about 0.1 Hz but cannot respond to the fluctuation when it has a high-frequency fluctuation of about 0.2 to 0.3 Hz. Hence, in a case in which the sympathetic nervous system increases its activity, the amount of frequency components of about 0.2 to 0.3 Hz is relatively small, as illustrated in FIG. 15A, when frequency components of the waveform for the heartbeat intervals are determined, and conversely, in a case in which the parasympathetic nervous system increases its activity, the amount of frequency components of about 0.2 to 0.3 Hz increases, as illustrated in FIG. 15B, relative to the case in FIG. 15A.

Accordingly, the ratio of low-frequency (LF) components to high-frequency (HF) components (i.e., LF/HF) can be used as an index indicating which of the sympathetic nervous system and the parasympathetic nervous system is dominant. When the LF/HF is large, the sympathetic nervous system is dominant, and when the LF/HF is small, the parasympathetic nervous system is dominant. Hence, when the sleepiness or the like occurs as the human state, and the parasympathetic nervous system increases its activity, the HF components increase as illustrated in FIG. 15B, and the LF/HF decreases. On the other hand, when stress or the like occurs to increase the activity of the sympathetic nervous system, the HF components decrease as illustrated in FIG. 15A, and the LF/HF increases. In this case, for example, it is assumed that the LF means frequency components of 0.15 Hz or lower and the HF means frequency components of 0.2 to 0.3 Hz. These boundary values are exemplary, and are not limited to the particular values.

The use of the above-described scheme allows the human state based on the autonomic nervous system to be estimated on the basis of the pulse wave detected by the skin-temperature and pulse-wave sensor 203. Although a scheme in which the pulse wave is detected from the earlobe part has been described above to detect the heartbeat intervals, the present disclosure is not limited to this scheme. For example, a sensor may be provided on a steering wheel or the like to detect the pulse wave from a fingertip portion or the like. Also, a method in which an electrocardiogram is measured instead of the pulse wave and the heartbeat intervals are extracted from the electrocardiogram may be used, and a method for detecting the pulse wave is not limiting, as long as the heartbeat intervals can be measured.

Next, a description will be given of a method for thermal sensation estimation using the skin temperature of a human peripheral part.

Figure 16:
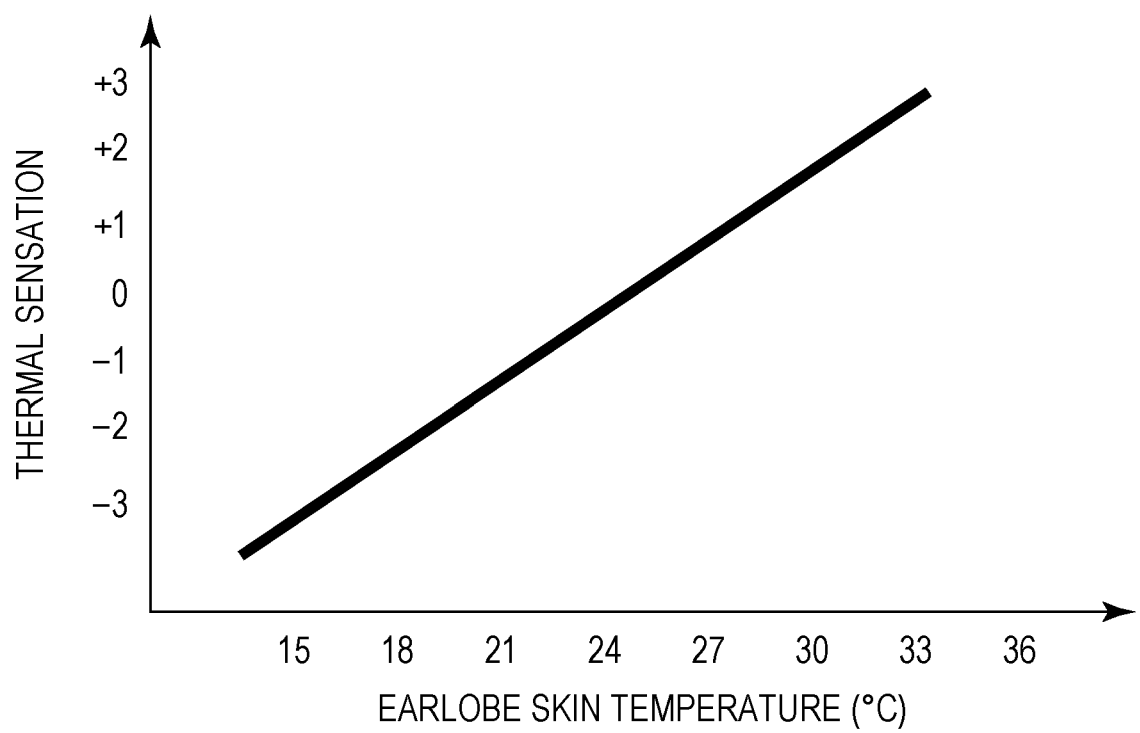
FIG. 16 is a correlation diagram illustrating one example of a correlation between an earlobe skin temperature and a thermal sensation in the second embodiment.

FIG. 16 is a correlation diagram illustrating one example of a correlation between an earlobe skin temperature and a thermal sensation in the present embodiment.

When the human feels cold, the brain tries to reduce the amount of blood that reaches the peripheral parts of the body by constricting the blood vessels of the peripheral parts in order to prevent a decrease in the temperature of the body core, which has many important organs for life sustenance. When the amount of blood that reaches the peripheral parts decreases, the skin temperatures of the peripheral parts decrease.

In contrast, when the human feels hot, the brain tries to increase the amount of blood that reaches the peripheral parts of the body by expanding the blood vessels of the peripheral parts in order to prevent the temperature of the body core from increasing to a certain temperature or more. When the amount of blood that reaches the peripheral parts increases, the skin temperatures of the peripheral parts increase.

As a result, a correlation occurs between the skin temperatures of the peripheral parts and the thermal sensation, for example, a linear correlation between the skin temperature of an earlobe part, which is a peripheral part, and the thermal sensation occurs, as illustrated in FIG. 16. Thus, detecting the skin temperature of a peripheral part makes it possible to estimate the human thermal sensation. Although a case in which the earlobe part is used as a peripheral part has been described above, it goes without saying any other peripheral part, such as a palm part or a nasal part, may be used. However, when human state estimation is performed in the vehicle 200, a lower body part of the person 202 is more likely to be affected by insolation. Thus, it is desirable to use the skin temperature of a part above the neck, and measuring the temperature at the nasal part or the earlobe part makes it possible to perform human state estimation that is less susceptible to disturbance due to insolation.

In addition, as illustrated in FIG. 16, the range of fluctuation in the skin temperature of a peripheral part, the fluctuation being caused by a variation (−3 to +3° C.) in the thermal sensation, is about 20° C. (i.e., about 15° C. to about 35° C.), which is large when compared with the range of temperature fluctuations (generally, about 1 to 2° C.) due to an influence of stress, sleepiness, or the like, which is another factor that affects the skin temperature. Thus, the range of fluctuations in the skin temperature of the peripheral part does not have a great influence on the thermal sensation to be estimated. Also, for example, the thermal sensation may be estimated based on a difference between the skin temperature of the forehead part or the like, the skin temperature being close to the skin temperature of the trunk portion, and the skin temperature of a peripheral part, not based only on the skin temperature of a peripheral part. By doing so, it is possible to reduce a personal difference during thermal sensation estimation.

Next, a description will be given of the configuration of a human-state estimating device 213 in the present embodiment.

Figure 17:
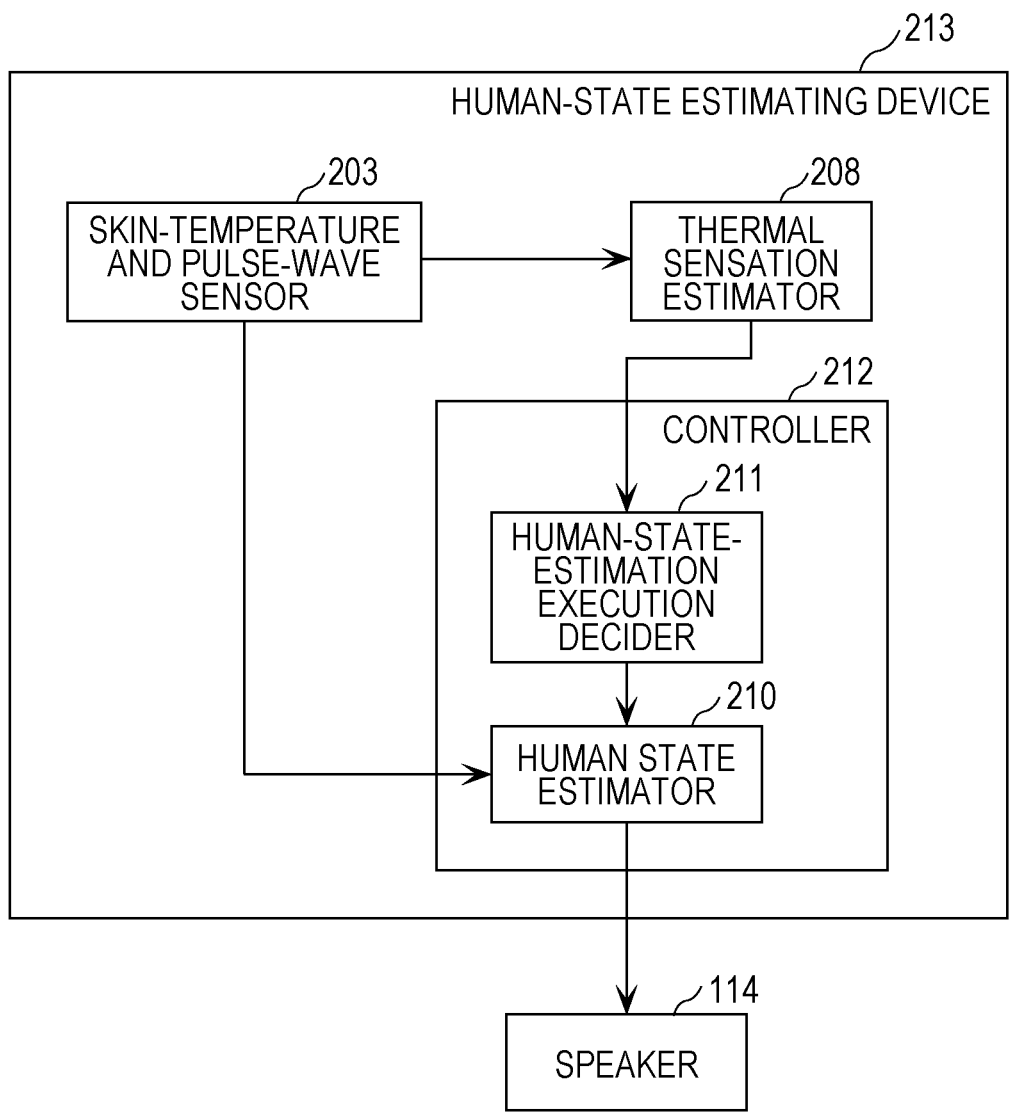
FIG. 17 is a block diagram illustrating functions of the human-state estimating device in the second embodiment.

FIG. 17 is a block diagram illustrating functions of the human-state estimating device 213 in the present embodiment.

The human-state estimating device 213 includes a skin-temperature and pulse-wave sensor 203, a thermal sensation estimator 208, and a controller 212.

The controller 212 includes a human state estimator 210 and a human-state-estimation execution decider 211.

The human state estimator 210 is a processor that estimates the degree of stress or sleepiness, which is a human state, on the basis of a pulse wave obtained by the skin-temperature and pulse-wave sensor 203. More specifically, the human state estimator 210 obtains heartbeat intervals of the person 202 as a physiological amount, the heartbeat intervals being obtained from the pulse wave, and estimates the human state of the person 202 on the basis of variations in the obtained heartbeat intervals.

The human-state-estimation execution decider 211 is a processor that decides whether or not the human state estimator 210 is to execute estimation of the human state. The human-state-estimation execution decider 211 is connected to the thermal sensation estimator 208, and a result of estimation of the thermal sensation of the person 202 is input to the human-state-estimation execution decider 211. The human-state-estimation execution decider 211 is connected to the human state estimator 210.

A flow of processing performed by the human-state estimating device 213 will be described below.

Figure 18:
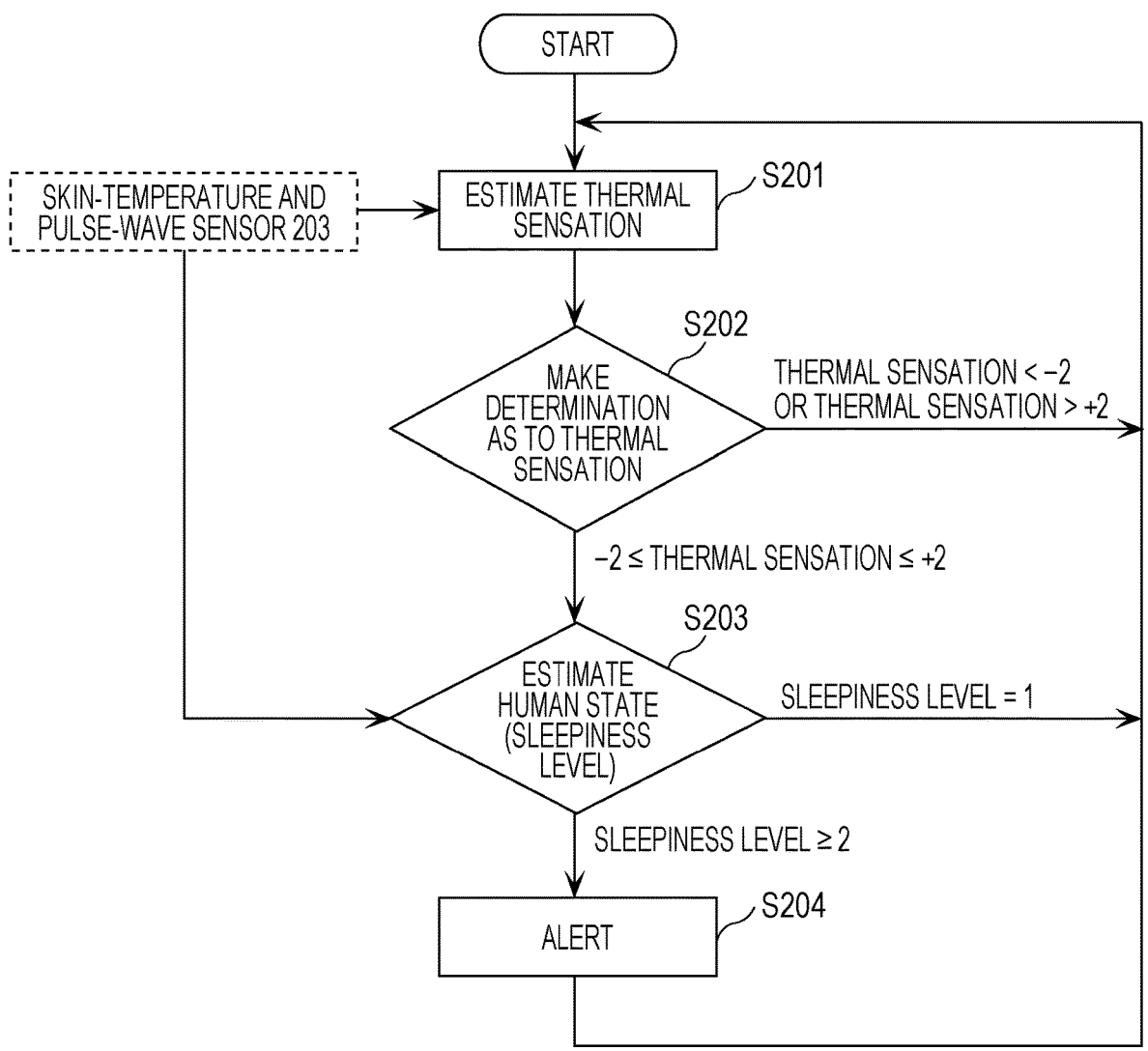
FIG. 18 is a flow diagram illustrating a method for human state estimation performed by the human-state estimating device in the second embodiment.

FIG. 18 is a flow diagram illustrating a method for human state estimation performed by the human-state estimating device 213 in the present embodiment.

In step S201, skin temperature data obtained by the skin-temperature and pulse-wave sensor 203 is input to the thermal sensation estimator 208, and the thermal sensation estimator 208 estimates the thermal sensation of the person 202.

In step S202, the thermal sensation of the person 202 which was estimated in step S201 is input to the human-state-estimation execution decider 211, and the human-state-estimation execution decider 211 makes a determination as to the thermal sensation.

If it is determined in step S202 that the thermal sensation is less than −2 or is more than +2, the process returns to step S201, and the thermal sensation estimator 208 estimates the thermal sensation of the person 202 again.

If it is determined in step S202 that the thermal sensation is in the range that is −2 or more and is +2 or less, the process proceeds to step S203.

In step S203, the human state estimator 210 estimates the sleepiness level as a human state, on the basis of the pulse wave measured by the skin-temperature and pulse-wave sensor 203. Also, a determination is made as to the estimated sleepiness level, and processing is performed in accordance with a result of the determination, as described below.

That is, if it is determined in step S203 that the sleepiness level is 1, the process returns to step S201, and then the series of processes illustrated in this flow diagram is performed again. In this case, since the sleepiness level is a level that does not affect driving the vehicle by the person 202, for example, it is thought that the person 202 does not need to be alerted.

On the other hand, if it is determined in step S203 that the sleepiness level is 2 or more, the person 202 is alerted. In this case, since it is thought that the sleepiness level is a level that affects driving the vehicle by the person 202, the alerting is performed in order to notify the person 202 about it. The alerting involves, for example, notifying the person 202 that the he or she is getting sleepy, urging the person 202 to take a rest, or the like by using the speaker 114. After the alerting, the process returns to step S201, and the series of processes illustrated in this flow diagram is performed again.

When the degree of stress is estimated as a human state, processing that is similar to that for the degree of sleepiness is performed with only a difference in the criterion for the determination made by the human state estimator 210, and thus descriptions thereof are not given hereinafter.

Thus, it is possible to determine whether a variation in the pulse wave is due to the human thermal sensation or due to sleepiness, thus making it possible to provide a high-accuracy degree-of-sleepiness estimating means. Naturally, the same applies to the degree of stress, which is a human state, and similarly, it is possible to provide a high-accuracy degree-of-stress estimating means. Thus, it is possible to provide a high-accuracy human-state estimating means. Also, for detecting the degree of sleepiness, for example, when the thermal sensation is −2 or less or is +2 or more, that is, when the human feels cold or hot, the human is less likely to feel sleepy. This makes it possible to omit unwanted estimation of the degree of sleepiness, the estimation being performed by the controller 112, and offers advantages that the processing load can be reduced and the energy consumed can be reduced.

Although the above description has been given of an example in which the human state estimator 210 estimates the sleepiness, and the person 202 is notified via the speaker 114 when the resulting sleepiness level is 2 or more, the means for notifying the person 202 is not limited thereto. For example, the seat belt may be fastened tight to urge the user to be awake or a warning may be displayed on a display or the like to notify the person 202, and the method for the notification is not particularly limiting.

In addition, although, in the human-state-estimation execution decider 211, the lower limit and the upper limit of the range of the thermal sensation determined by the thermal sensation estimator 208 are −2 and +2, respectively, the lower and upper limits may be different from these values. For example, the human state may be estimated using a thermal sensation that is −1 or more and is +1 or less. When this range includes the thermoneutral point and is small, the human state can be estimated with higher accuracy. Naturally, for example, decimal numbers, such as −1.5 and +1.5, rather than integers may be used as thresholds.

Although the description thus far has been given of an example of a case in which the thermal sensation estimator 208 automatically estimates the human thermal sensation, for example, the person 202 may directly input the thermal sensation of the person 202. As long as a value that enables determination of the thermal sensation of the person 202 can be provided to the human-state-estimation execution decider 211, the means therefor is not limiting.

Although the description thus far has been given of a case in which the human state is estimated based on the pulse wave, a description will be given of a method for higher-speed detection using respiration, mentioned in the first embodiment, in conjunction with the pulse wave.

Figure 19A:
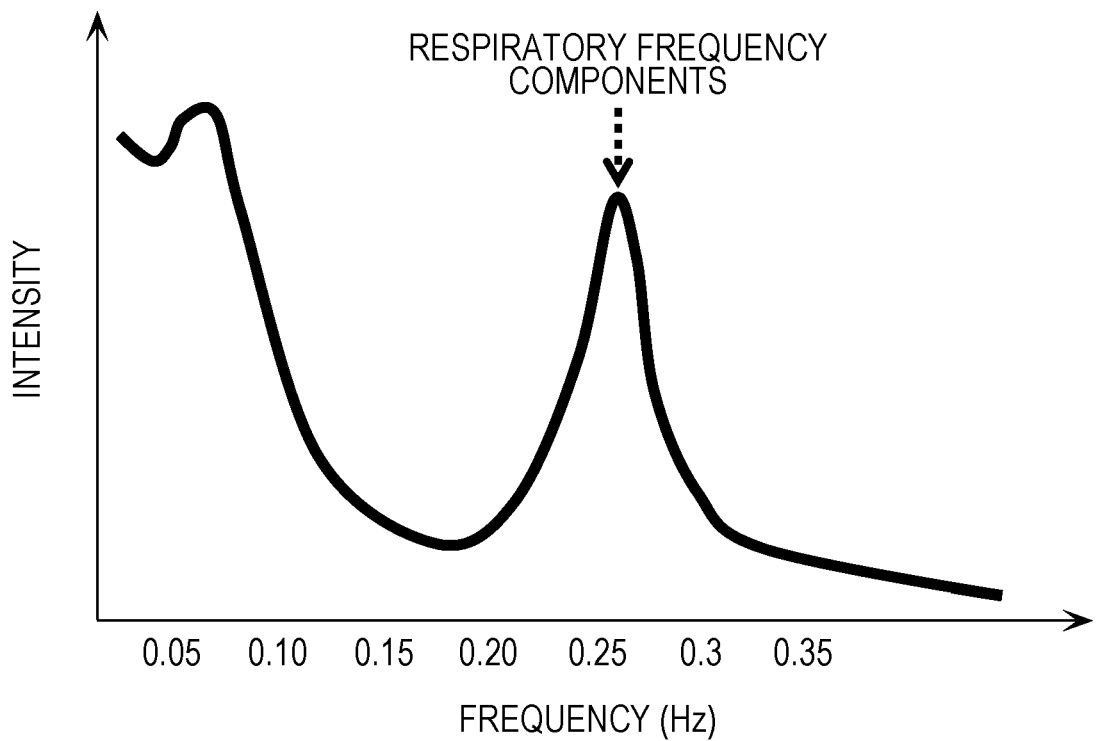
FIG. 19A is a graph illustrating a respiratory frequency according to a processing-load reducing method using respiratory components in the second embodiment.
Figure 19B:
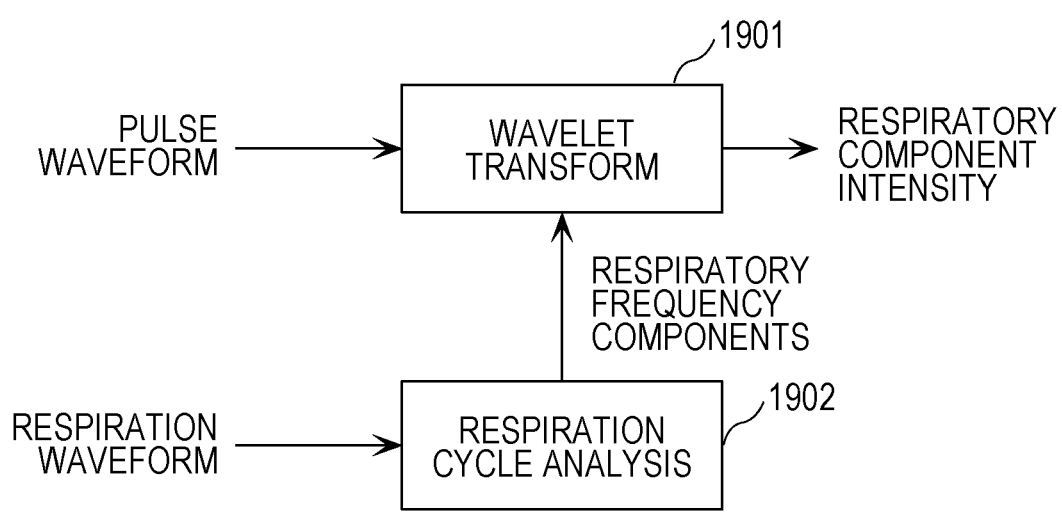
FIG. 19B is a block diagram illustrating a wavelet transform according to the processing-load reducing method using respiratory components in the second embodiment.

FIG. 19A is a graph illustrating a respiratory frequency according to a processing-load reducing method using respiratory components in the present embodiment. FIG. 19B is a block diagram illustrating a wavelet transform according to the processing-load reducing method using respiratory components in the present embodiment.

A case in which the frequency characteristics in FIGS. 15A and 15B are determined based on the heartbeat interval waveform illustrated in FIG. 14B has been described above with reference to FIGS. 15A and 15B. In general, such frequency characteristics are determined using a Fourier transform, a discrete Fourier transform, or the like, and when a computer is used, the frequency characteristics are determined using a fast Fourier transform in many cases. However, when a Fourier transform for the pulse wave is performed, only a piece of data is obtained therefrom in about a second, and thus there are cases in which data for about a few minutes is required. However, it is important that an approximate level of HF components be detected for LF/HF analysis for analyzing the autonomic nervous system, and detecting all frequency components is not necessarily required.

Accordingly, a respiration waveform can be utilized as a physiological amount, as illustrated in FIG. 19B. That is, the human state can be estimated based on the respiration waveform in addition to the heartbeat intervals. The respiration waveform may be determined by using temperature fluctuations of the nostril parts, as described above in the first embodiment. The respiration waveform may be determined by any other means, for example, by detecting abdominal-part expansion or contraction due to respiration on the basis of the tension of the seat belt or by detecting a change in the position of the abdominal part in a contactless manner by using a millimeter wave or the like. Respiration cycle analysis 1902 is performed on the obtained respiration waveform, and for example, a respiration cycle is analyzed based on the interval between peak values to thereby determine the frequency of respiratory frequency components of the person 202. Next, a wavelet transform 1901 is performed on the obtained pulse waveform to determine the intensity of respiratory frequency components obtained from the respiration waveform.

By extracting the respiratory component intensity of the pulse wave on the basis of the respiration waveform, it is possible to determine an approximate level of the respiratory frequency components included in the pulse wave in less than one minute. The amount of computation involved in this method is smaller than the amount of computation involved in a Fourier transform, thus offering advantages in that it is possible to reduce the amount of processing load on the human-state estimating device 213 to thereby reduce the energy consumed.

A description will be given of a human-state estimating method when a respiration sensor is also used.

Figure 20:
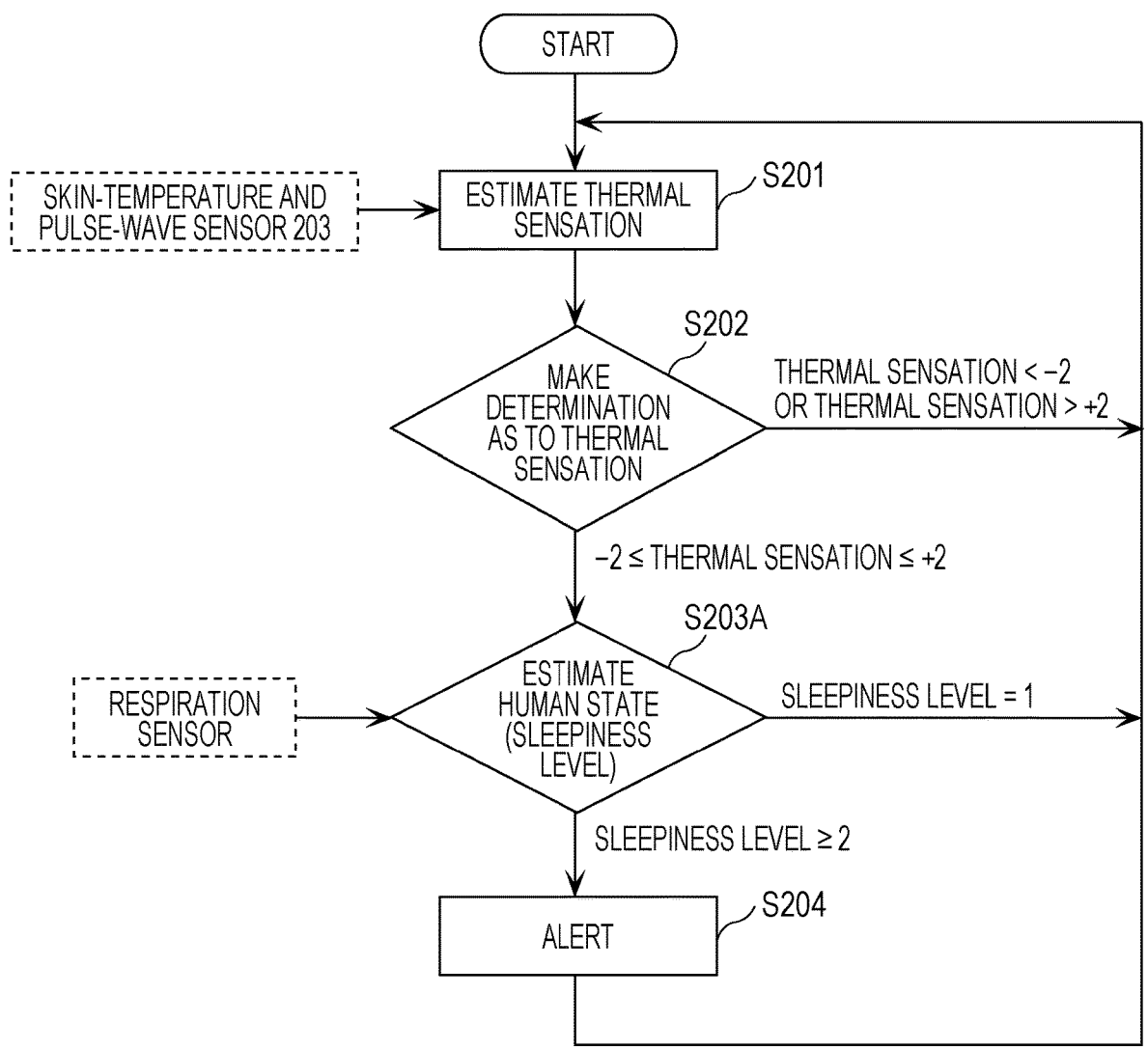
FIG. 20 is a flow diagram illustrating a human-state estimating method employing the processing-load reducing method using respiratory components in the second embodiment.

FIG. 20 is a flow diagram illustrating a human-state estimating method employing the processing-load reducing method using respiratory components in the present embodiment.

In step S203A, a respiration waveform obtained by a respiration sensor, in addition to the pulse wave obtained by the skin-temperature and pulse-wave sensor 203, is input as an input for estimating the human state of the human state estimator 210.

Since other steps are substantially the same as the processing steps having the same names in FIG. 18, detailed descriptions thereof are not given hereinafter.

In FIGS. 13A and 13B, the skin-temperature and pulse-wave sensor 203 is attached to the left ear of the person 202. However, when the vehicle 200 is a right-hand drive vehicle, it is desirable that the skin-temperature and pulse-wave sensor 203 be attached to the left ear, since the person 202 is less likely to be affected by disturbance, such as insolation. Also, when a pulse wave is optically detected, the person 202 is less likely be affected by disturbance, such as insolation. Naturally, when the vehicle 200 is a left-hand drive vehicle, it is desirable that the skin-temperature and pulse-wave sensor 203 be attached to the right ear.

A scheme for detecting a pulse wave from the earlobe part has been described in the present embodiment. However, for example, when the human state of a person who is working with a personal computer or the like in an office or the like is detected based on a pulse wave, the pulse wave may be detected via a mouse, which is an input device for the personal computer, not via the earlobe. The portions of the mouse where the fingers are placed are generally determined, and thus, when the mouse is configured so as to optically read a pulse wave at any of the portions, it is possible to detect the human state without the person 202 actively wearing a sensor. Besides, a wearable sensor, for example, an element for detecting a human pulse wave, may be attached to a shirt or the like to wirelessly transfer a pulse waveform to a smartphone or the like, and the pulse waveform may be processed using a cloud server or the like. This arrangement makes it possible to detect the human state even when the person is moving. Also, for example, when the human states of a large number of people are treated as big data and are analyzed, it is possible to identify places or time segments in which people feel much stress, thus making it possible to extract places or time segments in which accidents or the like are more likely to occur.

Next, a description will be given of a method for reducing a personal difference in the human state.

Figure 21:
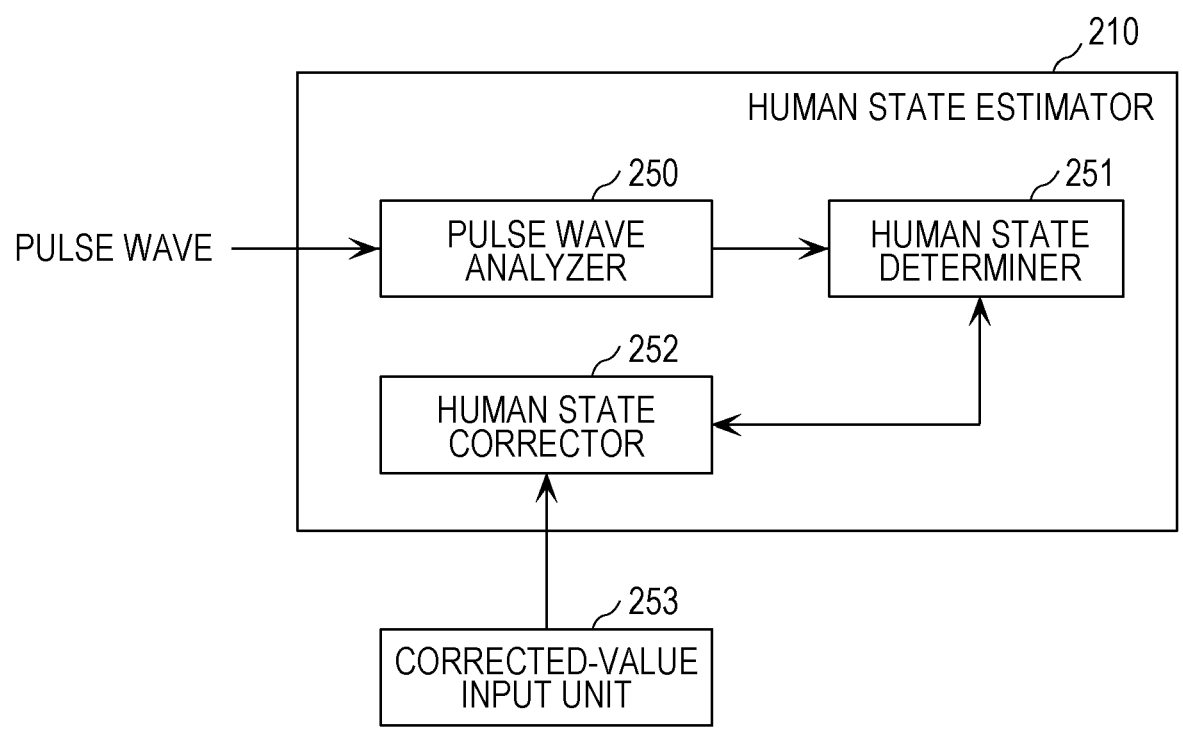
FIG. 21 is a block diagram illustrating a function for correcting a human state determination result in the second embodiment.

FIG. 21 is a block diagram illustrating a function for correcting a human state determination result in the present embodiment.

When the human state estimator 210 is to determine the human state through analysis of a pulse wave, a pulse wave analyzer 250 performs the above-described Fourier transform and wavelet transform to determine the LF/HF, and a human state determiner 251 determines at which of levels 1 to 5 the degree of sleepiness, which is the human state, is, on the basis of the value of the LF/HF. A speaker or the like outputs sound indicating the result of the determination.

The person 202 will know the result of the determination by listening thereto. When the person 202 thinks that the determined human state and the degree of sleepiness he or she feels differ from each other, he or she inputs, via a corrected-value input unit 253, the degree of sleepiness he or she feels. A human state corrector 252 recognizes a personal difference on the basis of the degree of sleepiness determined by the human state determiner 251 and the person's degree of sleepiness received by the corrected-value input unit 253 and stores the personal difference. Thereafter, the human state corrector 252 uses the value of the stored personal difference to correct the result of the determination made by the human state determiner 251, thereby estimating the human state corrected for the individual person 202. With this arrangement, it is possible to provide a human-state estimating device 213 with a small personal difference.

Although the description thus far has been given of the human state detector using the skin temperature and the pulse wave, the present disclosure is not limited thereto. For example, a skin blood flow rate, other than the skin temperature and the pulse wave, may be detected, and means for the detection is not limiting, as long a physiological amount, such as a line-of-sight, blinking, a cerebral blood flow, or a brain wave, controlled by the autonomic nervous system is obtained.

As described above, in the human-state estimating method according to the present embodiment, false detection during human state estimation is reduced to thereby make it possible to estimate the human state with higher accuracy. More specifically, in the human-state estimating method according to one aspect of the present disclosure, the human state is estimated based on a physiological amount under a situation in which the condition that the obtained thermal sensation information is in the predetermined range is satisfied. Thus, false detection during human state estimation can be reduced, compared with a case in which the human state is estimated regardless of whether or not the condition is satisfied. Accordingly, the above-described human-state estimating method makes it possible to improve the accuracy of estimating the human state. In addition, a reduction of false detection eliminates the need for performing the detection processing again, thus offering advantages in that the throughput, the processing load, and the amount of power consumed decrease.

Additionally, the human state can be specifically estimated based on the human heartbeat intervals.

Also, the human state can be specifically estimated based on the human respiration waveform. This can also contribute to reducing the processing load and increasing the processing speed.

Moreover, the human state can be specifically estimated based on the skin temperature and the pulse wave of the human earlobe part. The earlobe part has a feature that the pulse wave can be easily measured. Accordingly, when a pulse wave is obtained from the earlobe part in conjunction with the skin temperature, information needed for estimating the human state can be obtained from the earlobe part at a time.

In each embodiment described above, although the constituent elements are implemented by dedicated hardware, the constituent elements may also be realized by executing a software program that suits the constituent elements. A program executor, such as a central processing unit (CPU) or a processor, may read and execute the software program recorded on/in a recording medium, such as a hard disk or a semiconductor memory, to thereby realize the constituent elements. Herein, software for realizing the human-state estimating device in each embodiment described above is a program as described below.

That is, this program causes a computer to execute a human-state estimating method including: obtaining a thermal sensation index obtained by indexing, in a specified range, an estimated thermal sensation of a person; determining whether or not the obtained thermal sensation index is in a predetermined range in the specified range; and estimating a human state, which is a state of the person, based on a physiological amount in which an activity of an autonomic nervous system of the person is reflected, the physiological amount being obtained when it is determined that the obtained thermal sensation index is in the predetermined range.

Although the human-state estimating device and so on according to one or more aspects have been described above based on the embodiments, the present disclosure is not limited to the embodiments. A mode obtained by making various modifications conceived by those skilled in the art to the embodiments or a mode implemented by combining the constituent elements in a different embodiment may also be encompassed by the scope of one or more aspects, as long as such modes do not depart from the spirit and scope of the present disclosure.

For example, the present disclosure encompasses the following cases.

(1) In the above embodiments, the description has been given of a human-state estimating scheme using at least the sensors, the thermal sensation estimator, and the controller. However, the sensors, the thermal sensation estimator, the controller, and some of the constituent elements used for the human-state estimating scheme can also be individually configured as software. In this case, a main element that processes the software may be a calculator used for the human-state estimating scheme, may be a calculator included in a personal computer (PC), a smartphone, or the like, or may be a cloud server or the like connected to the human-state estimating device over a network.

In addition, the arrangement or the configuration of the individual devices are not limited to the arrangement or the configuration as illustrated in FIG. 3. Some or all of the sensors (the camera, the thermometer, the globe thermometer, the anemometer, and the hygrometer) may be incorporated into a single module or may be arranged as independent units. Also, the thermal sensation estimator 108 may be incorporated into the human-state estimating device 113 as a single unit, as illustrated in FIG. 10. The thermal-sensation estimation controller 106 (or processing realized thereby) may be provided individually as software. Also, the thermal sensation estimator 108 and the controller 112 (or processing realized thereby) may be provided as a single piece of software. In addition, the thermal image sensor 101, the thermal-sensation estimation controller 106, and the controller 112 may be provided as a single module. The arrangement or the configuration of the individual devices are not limited to those described above, and it is to be noted that the present disclosure encompasses a mode in which the constituent elements combined in any way are provided as software or a module.

(2) Each device described above may be, specifically, a computer system including a microprocessor, a read-only memory (ROM), a random-access memory (RAM), a hard disk unit, a display unit, a keyboard, a mouse, and so on. A computer program is stored in the RAM or the hard disk unit. The microprocessor operates in accordance with the computer program, so that each device realizes its functions. The computer program in this case is made of a combination of a plurality of instruction codes for giving instructions to a computer in order to achieve a predetermined function.

(3) Some or all of the constituent elements included in each device described above may be implemented by one system large-scale-integrated (LSI) circuit. The system LSI is a super-multifunctional LSI manufactured by integrating a plurality of constituent elements on one chip and is, specifically, a computer system including a microprocessor, a ROM, a RAM, and so on. The computer program is stored in the RAM. The microprocessor operates in accordance with the computer program, so that the system LSI realizes its functions.

(4) Some or all of the constituent elements included in each device described above may be implemented by an integrated circuit (IC) card or a single module that can be inserted into and removed from the device. The IC card or the module may be a computer system including a microprocessor, a ROM, a RAM, and so on. The IC card or the module may include the aforementioned super-multifunctional LSI. The microprocessor operates in accordance with the computer program, so that the IC card or the module realizes its functions. The IC card or the module may be tamper-proof.

(5) The present disclosure may also be implemented by the methods described above. Those methods may also be realized by a computer program implemented by a computer or may be realized using digital signals provided by the computer program.

In the present disclosure, the computer program or the digital signals may be recorded on computer-readable recording media, for example, a flexible disk, a hard disk, a CD-ROM, a magneto-optical (MO) disk, a digital versatile disk (DVD), a DVD-ROM, a DVD-RAM, a Blu-ray® Disc (BD), and a semiconductor memory. Those methods may also be realized by the digital signals recorded on the recording media.

Additionally, in the present disclosure, the computer program or the digital signals may be transmitted over a telecommunication channel, a wireless or wired communication channel, a network typified by the Internet, data broadcasting, or the like.

Moreover, the present disclosure may be realized by a computer system including a microprocessor and a memory, the memory may store the computer program, and the microprocessor may operate in accordance with the computer program.

The present disclosure may also be implemented by another independent computer system by transporting the recording medium on which the program or the digital signals are recorded or transferring the program or the digital signals over the network or the like.

(6) The above-described embodiments and the modifications may also be combined together.

The present disclosure can be applied to a human-state estimating device and particularly to a human-state estimating device for estimating the state of a person in the driver's seat of a vehicle or a train, in an office, or the like.

What is claimed is:

1. A human-state estimating method comprising:
estimating, using a processor, a thermal sensation of a person,
wherein the thermal sensation is estimated based on a skin temperature of a peripheral part of the person's body output from a sensor, being put on the peripheral part of the person's body, that detects the skin temperature of the peripheral part of the person's body, or
wherein the thermal sensation is estimated based on (i) a state of a space including a person which is output from a sensor that detects, as the state of the space, a temperature in the space, a radiant temperature in the space, a wind speed in the space or a humidity in the space and (ii) an amount of clothing worn by the person which is obtained from an image output by a camera that captures the person;
obtaining, using the processor, a thermal sensation index obtained by indexing the estimated thermal sensation of the person, in a specified range, the specified range including a thermoneutral point for thermal sensation; and
estimating a human state, using the processor, which is a state of the person, based on a physiological amount in which an activity of an autonomic nervous system of the person is reflected, the physiological amount being obtained from a sensor when it is determined that the obtained thermal sensation index is in a predetermined range in the specified range,
wherein if the obtained thermal sensation index is determined to be outside the predetermined range, the processor does not estimate the human state of the person.

2. The human-state estimating method according to claim 1,
wherein the predetermined range is a partial range of the specified range, the partial range including a thermoneutral point for thermal sensation.

3. The human-state estimating method according to claim 1,
wherein the predetermined range is a partial range of the specified range, the partial range not including a point indicating being hottest as the thermal sensation and a point indicating being coldest as the thermal sensation.

4. The human-state estimating method according to claim 1,
wherein the physiological amount comprises a nasal skin temperature of the person, and
the human state comprises a degree of sleepiness of the person.

5. The human-state estimating method according to claim 4,
wherein the nasal skin temperature is obtained from the sensor;
determining whether or not the obtained thermal sensation index is in the predetermined range; and
in the estimating of the human state, the degree of sleepiness of the person is estimated based on a range of an increase in the obtained nasal skin temperatures over time.

6. The human-state estimating method according to claim 1,
wherein the physiological amount comprises a heartbeat interval of the person; and
the human state is estimated based on a variation in the heartbeat interval as the physiological amount obtained from the sensor.

7. The human-state estimating method according to claim 6,
wherein the physiological amount comprises a respiration waveform of the person; and
the human state is estimated based on the respiration waveform as the physiological amount obtained from the sensor.

8. The human-state estimating method according to claim 1,
wherein a skin temperature of an earlobe part of the person is obtained;
in the obtaining of the thermal sensation index, a correlation between a skin temperature of an earlobe part and the thermal sensation index is used to obtain the thermal sensation index estimated based on the obtained skin temperature of the earlobe part;
the physiological amount, obtained from the sensor, comprises a pulse wave measured from the earlobe part of the person; and
in the estimating of the human state, the human state is estimated based on frequency analysis of the obtained pulse wave.

9. The human-state estimating method according to claim 1,
wherein in the obtaining of the thermal sensation index, the thermal sensation index estimated based on a predicted mean vote (PMV) is obtained.

10. The human-state estimating method according to claim 9,
wherein the specified range is represented by a seven-step evaluation scale for the PMV; and
the predetermined range is a range in which a PMV value is −2 or more and is +2 or less in the specified range.

11. The human-state estimating method according to claim 1, wherein
the physiological amount comprises a nasal skin temperature of the person;
the human state comprises a degree of stress of the person;
the nasal skin temperature is obtained from the sensor;
the method further comprises determining whether or not the thermal sensation index obtained by the obtaining, is in the predetermined range; and
in the estimating of the human state, the degree of stress of the person is estimated based on a range of a decrease in the obtained nasal skin temperatures over time.

12. The human-state estimating method according to claim 1,
wherein the physiological amount comprises a skin blood flow, a blood pressure, or a pulse-wave propagation time of the person; and
the human state comprises a degree of sleepiness of the person.

13. The human-state estimating method according to claim 1, further comprising determining whether or not the obtained thermal sensation index is in the predetermined range in the specified range, the predetermined range being a range of the thermal sensation equal or close to the thermoneutral point.

14. A non-transitory recording medium storing a program causing a computer to execute operations comprising:
estimating, using a processor of the computer, a thermal sensation of a person,
wherein the thermal sensation is estimated based on a skin temperature of a peripheral part of the person's body output from a sensor, being put on the peripheral part of the person's body, that detects the skin temperature of the peripheral part of the person's body, or
wherein the thermal sensation is estimated based on (i) a state of a space including a person which is output from a sensor that detects, as the state of the space, a temperature in the space, a radiant temperature in the space, a wind speed in the space or a humidity in the space and (ii) an amount of clothing worn by the person which is obtained from an image output by a camera that captures the person;
obtaining, using the processor, a thermal sensation index obtained by indexing the estimated thermal sensation of the person, in a specified range, the specified range including a thermoneutral point for thermal sensation; and
estimating a human state, using the processor, which is a state of the person, based on a physiological amount in which an activity of an autonomic nervous system of the person is reflected, the physiological amount being obtained from a sensor when it is determined that the obtained thermal sensation index is in a predetermined range in the specified range,
wherein if the obtained thermal sensation index is determined to be outside the predetermined range, the processor does not estimate the human state of the person.

15. The non-transitory recording medium storing a program according to claim 14, the executed operations further comprising determining whether or not the obtained thermal sensation index is in the predetermined range in the specified range, the predetermined range being a range of the thermal sensation equal or close to the thermoneutral point.

* * * * *